US010071230B2

(12) United States Patent
Sela et al.

(10) Patent No.: US 10,071,230 B2
(45) Date of Patent: Sep. 11, 2018

(54) SENSOR MOUNTED FLEXIBLE GUIDEWIRE

(71) Applicant: MediGuide, Ltd., Haifa (IL)

(72) Inventors: Ran Sela, Tel Aviv-Jaffa (IL); Dan Seter, Haifa (IL); Nimrod Meller, Kiryat Tivon (IL)

(73) Assignee: MEDIGUIDE LTD., Haifa (IL)

( * ) Notice: Subject to any disclaimer, the term of this patent is extended or adjusted under 35 U.S.C. 154(b) by 0 days.

(21) Appl. No.: 14/815,671

(22) Filed: Jul. 31, 2015

(65) Prior Publication Data

US 2016/0030718 A1 Feb. 4, 2016

Related U.S. Application Data

(60) Division of application No. 12/981,631, filed on Dec. 30, 2010, now Pat. No. 9,095,685, which is a
(Continued)

(51) Int. Cl.
*A61B 5/00* (2006.01)
*A61M 25/09* (2006.01)
(Continued)

(52) U.S. Cl.
CPC ............. *A61M 25/09* (2013.01); *A61B 5/01* (2013.01); *A61B 5/06* (2013.01); *A61B 5/065* (2013.01);
(Continued)

(58) Field of Classification Search
CPC .. A61B 5/06; A61B 5/01; A61B 5/065; A61B 5/6851; A61B 18/1492;
(Continued)

(56) References Cited

U.S. PATENT DOCUMENTS 2,452,679 A 11/1948 Ramsden
2,483,900 A 10/1949 Hardenberg et al.
(Continued)

FOREIGN PATENT DOCUMENTS

EP 0894473 2/1999
JP 2008-112289 5/1996
(Continued)

*Primary Examiner* — May Abouelela
(74) *Attorney, Agent, or Firm* — Dykema Gossett PLLC

(57) ABSTRACT

A medical device comprising a corewire, sensor core, and coupler is presented. A portion of the corewire is disposed within a first end of the coupler, and a portion of the sensor core is disposed within a second end. Alternatively, the device comprises a corewire and a sensor assembly comprising a sensor core having first and second ends and a bore in the first end. A portion of the corewire is disposed within the bore. A method of manufacture comprises providing a corewire, sensor core, and coupler. The method further comprises inserting a portion of the corewire into a first end of the coupler, and a portion of the sensor core into a second end. Alternatively, the method comprises providing a sensor core having first and second ends, and a corewire. The method further comprises forming a bore in the first end, and inserting the corewire into the bore.

21 Claims, 22 Drawing Sheets

Related U.S. Application Data continuation-in-part of application No. 12/357,971, filed on Jan. 22, 2009, now Pat. No. 8,443,076.

(60) Provisional application No. 61/023,007, filed on Jan. 23, 2008, provisional application No. 61/028,665, filed on Feb. 14, 2008.

(51) Int. Cl.
  *A61B 5/06* (2006.01)
  *A61B 5/01* (2006.01)
  *A61M 25/00* (2006.01)
  *A61B 34/20* (2016.01)

(52) U.S. Cl.
  CPC ....... *A61B 5/6851* (2013.01); *A61M 25/0905* (2013.01); *A61B 2034/2051* (2016.02); *A61M 2025/0002* (2013.01); *A61M 2025/0915* (2013.01); *A61M 2025/09083* (2013.01); *A61M 2025/09108* (2013.01); *A61M 2025/09133* (2013.01); *A61M 2025/09175* (2013.01); *A61M 2025/09183* (2013.01); *A61M 2205/3515* (2013.01)

(58) Field of Classification Search
  CPC ............... A61B 34/20; A61B 18/1815; A61B 2034/2051; A61B 2017/22038; A61B 2018/00404; A61B 5/0422; A61M 25/09; A61M 25/0905; A61M 2934/2051; A61M 2025/0166
  USPC ................................................. 600/585, 300
  See application file for complete search history.

(56) References Cited

U.S. PATENT DOCUMENTS

| | | |
|---|---|---|
| 4,873,986 A | 10/1989 | Wallace |
| 4,991,602 A | 2/1991 | Amplatz |
| 5,386,828 A | 2/1995 | Owens et al. |
| 5,445,151 A | 8/1995 | Darrow |
| 5,501,228 A | 3/1996 | Lafontaine |
| RE35,648 E | 11/1997 | Tenerz |
| 5,728,062 A | 3/1998 | Brisken |
| 5,850,682 A | 12/1998 | Ushiro |
| 5,868,674 A | 2/1999 | Glowinski |
| 5,873,835 A | 2/1999 | Hastings et al. |
| 6,007,478 A | 12/1999 | Sless |
| 6,090,052 A | 7/2000 | Akerfeldt et al. |
| 6,106,486 A | 8/2000 | Tenerz |
| 6,112,598 A | 9/2000 | Tenerz |
| 6,142,958 A | 11/2000 | Hammarstrom |
| 6,261,246 B1 | 7/2001 | Pantages et al. |
| 6,353,379 B1 | 3/2002 | Busletta et al. |
| 6,375,606 B1 | 4/2002 | Garibaldi |
| 6,428,336 B1 | 8/2002 | Akerfeldt |
| 6,428,489 B1 | 8/2002 | Jacobsen et al. |
| 6,442,413 B1 | 8/2002 | Silver |
| 6,675,033 B1 | 1/2004 | Lardo |
| 6,711,429 B1 | 3/2004 | Gilboa et al. |
| 6,847,837 B1 | 1/2005 | Melzer |
| 6,862,467 B2 | 3/2005 | Moore et al. |
| 7,011,636 B2 | 3/2006 | Tenerz |
| 7,048,716 B1 | 5/2006 | Kucharczyk |
| 7,130,700 B2 | 10/2006 | Gardeski et al. |
| 7,162,293 B2 | 1/2007 | Weiss |
| 7,169,118 B2 | 1/2007 | Reynolds et al. |
| 7,186,209 B2 | 3/2007 | Jacobson |
| 7,197,354 B2 | 3/2007 | Sobe |
| 7,645,233 B2 | 1/2010 | Tulkki |
| 7,951,081 B2 | 5/2011 | Hamm et al. |
| 8,239,003 B2 | 8/2012 | Akins |
| 8,343,076 B2 | 1/2013 | Sela |
| 8,579,825 B2 | 11/2013 | Tenerz et al. |
| 2001/0051769 A1 | 12/2001 | Hoek |
| 2002/0009535 A1 | 1/2002 | Michael et al. |
| 2002/0032390 A1 | 3/2002 | Jafari |
| 2002/0151823 A1 | 10/2002 | Mlyata et al. |
| 2003/0028128 A1 | 2/2003 | Tenerz |
| 2003/0073898 A1 | 4/2003 | Weiss |
| 2003/0120146 A1 | 6/2003 | Dumoulin |
| 2003/0120148 A1 | 6/2003 | Pacetti |
| 2003/0139689 A1 | 7/2003 | Shturman et al. |
| 2003/0199852 A1 | 10/2003 | Seward et al. |
| 2003/0220588 A1 | 11/2003 | Tenerz et al. |
| 2004/0102720 A1 | 5/2004 | Kellerman et al. |
| 2004/0116800 A1 | 6/2004 | Helfer |
| 2004/0167436 A1 | 8/2004 | Reynolds et al. |
| 2004/0167442 A1 | 8/2004 | Shireman et al. |
| 2004/0220462 A1 | 11/2004 | Schwartz |
| 2004/0254458 A1 | 12/2004 | Govari |
| 2004/0260172 A1 | 12/2004 | Ritter |
| 2005/0049523 A1 | 3/2005 | Crank |
| 2005/0059852 A1 | 3/2005 | Rioux |
| 2005/0059861 A1* | 3/2005 | Nishiie ............... A61B 1/00071 600/144 |
| 2005/0070793 A1 | 3/2005 | Pacetti et al. |
| 2005/0148901 A1* | 7/2005 | Parins .................. A61M 25/09 600/585 |
| 2006/0084867 A1 | 4/2006 | Tremblay |
| 2006/0178576 A1 | 8/2006 | Weber |
| 2007/0185386 A1 | 8/2007 | Cheng |
| 2007/0208251 A1 | 9/2007 | Anderson |
| 2007/0255144 A1 | 11/2007 | Tulkki et al. |
| 2007/0255145 A1 | 11/2007 | Smith et al. |
| 2008/0097247 A1 | 4/2008 | Eskuri |
| 2008/0121242 A1 | 5/2008 | Revie et al. |
| 2008/0194991 A1* | 8/2008 | Teague .................. A61M 25/09 600/585 |
| 2008/0200770 A1 | 8/2008 | Hubinette |
| 2009/0112128 A1 | 4/2009 | Schiff |
| 2009/0143777 A1 | 6/2009 | Pacey |
| 2009/0177119 A1 | 7/2009 | Heidner et al. |
| 2009/0209900 A1 | 8/2009 | Carmell |
| 2010/0217275 A1 | 8/2010 | Carmell |
| 2010/0286536 A1 | 11/2010 | Samuelsson |
| 2011/0152721 A1 | 6/2011 | Sela |
| 2012/0203118 A1 | 8/2012 | Samuelsson |
| 2012/0265079 A1 | 10/2012 | Hilmersson |
| 2013/0102892 A1 | 4/2013 | Strommer |
| 2013/0102927 A1 | 4/2013 | Hilmersson |
| 2013/0338538 A1 | 12/2013 | Park |
| 2014/0276138 A1 | 9/2014 | Millett |

FOREIGN PATENT DOCUMENTS

| | | |
|---|---|---|
| JP | 2003-024447 | 1/2003 |
| JP | 2006-150082 | 6/2006 |
| WO | 1996/005768 | 2/1996 |

\* cited by examiner

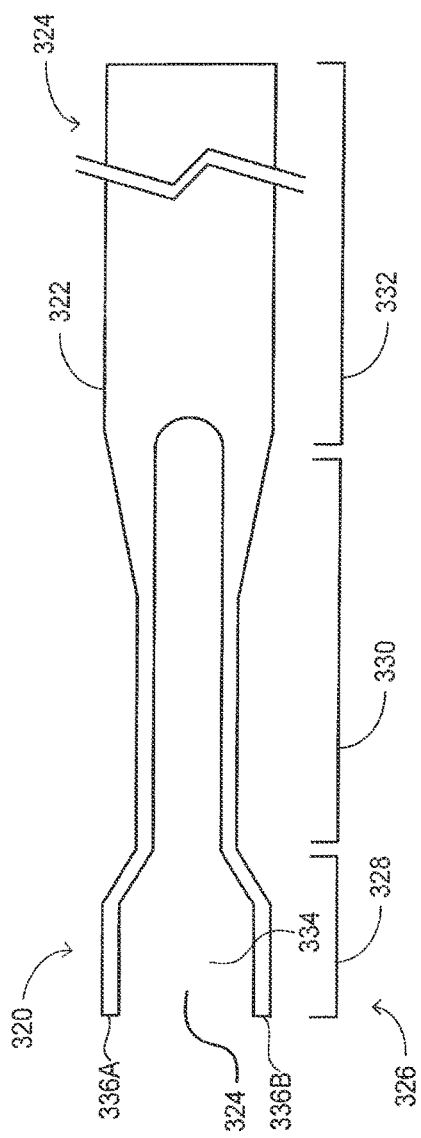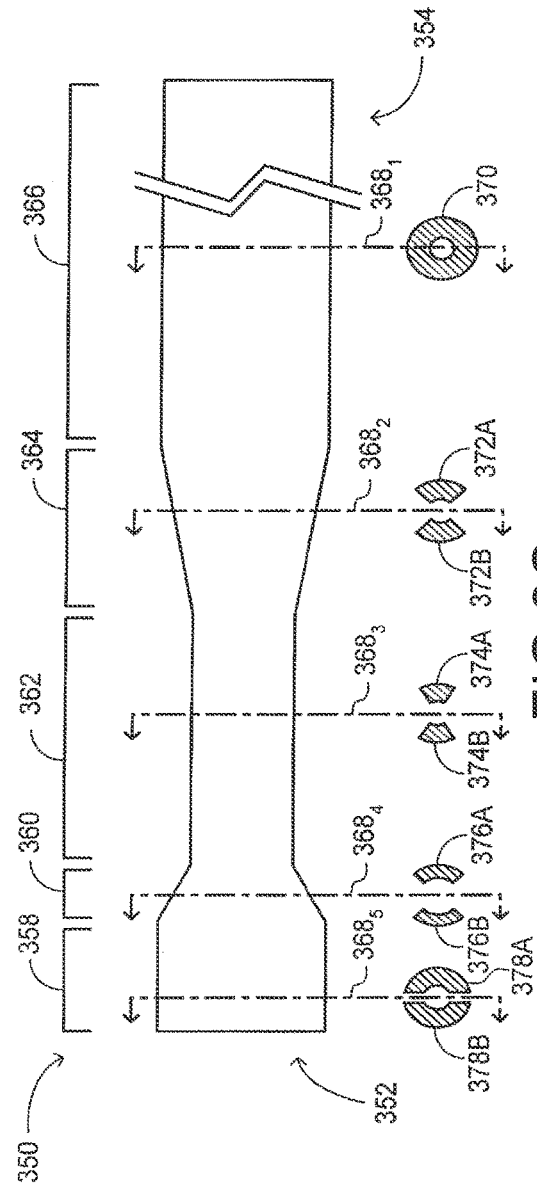
FIG.3B
FIG.3C

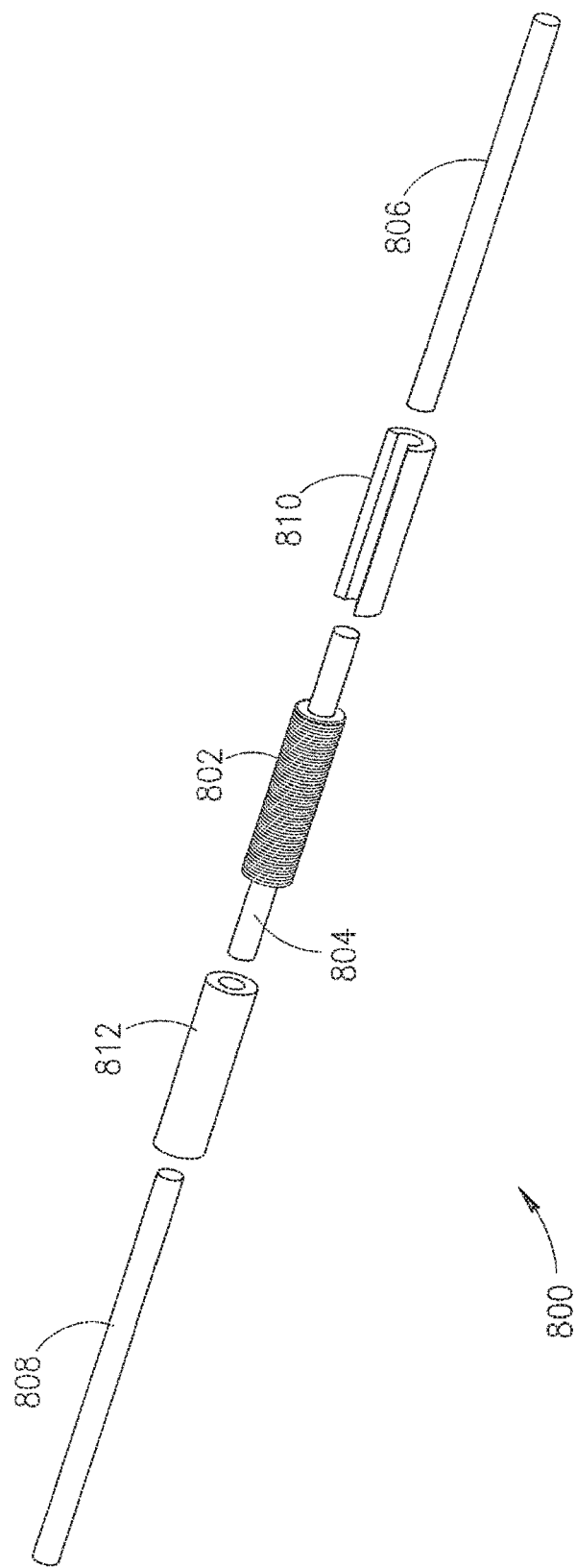

SENSOR MOUNTED FLEXIBLE GUIDEWIRE

CROSS REFERENCE TO RELATED APPLICATIONS

This application is a divisional of U.S. application Ser. No. 12/981,631, filed 30 Dec. 2010 (the '631 application), now U.S. Pat. No. 9,095,685, which is a continuation-in-part of U.S. application Ser. No. 12/357,971, filed 22 Jan. 2009 (the '971 application), now U.S. Pat. No. 8,343,076, which claims the benefit of U.S. provisional application No. 61/023,007, filed 23 Jan. 2008 (the '007 application) and U.S. provisional application No. 61/028,665, filed 14 Feb. 2008 (the '665 application). The '631 application, the 971 application, the '007 application, and the '665 application are all hereby incorporated by reference as though fully set forth herein.

BACKGROUND OF THE INVENTION a. Field of the Invention

The disclosed technique relates to guidewires, in general, and to methods and systems for including electronic components in guidewires and for making guidewires more flexible, in particular.

b. Background Art

Guidewires are employed in noninvasive operations to enable the physician to navigate to a desired location within the lumen of the body of the patient, and then insert the catheter to the desired location with the aid of the guidewire. Such guidewires are known in the art. One type of guidewire includes a sensor at the tip thereof, which is connected to an electronic unit, with a pair of wires which pass through a lumen within the guidewire. The guidewire includes a coil in front of the sensor to enable maneuverability. Another type of guidewire includes a sensor at the tip thereof, which is connected to the electronic unit with a pair of wires which pass through the lumen within the guidewire. This guidewire is devoid of a flexible element to provide maneuverability.

U.S. Pat. No. Re. 35,648 issued to Tenerz et al., and entitled "Sensor Guide Construction and Use Thereof," is directed to a guidewire which includes a thin outer tube, an arched tip, a radiopaque coil, a solid metal wire, a sensor element, and a signal transmitting cable. The radiopaque coil is welded to the arched tip. The solid metal wire is formed like a thin conical tip, and it is located within the arched tip and the radiopaque coil. The solid metal wire successively tapers toward the arched tip. At the point where the solid metal wire joins the radiopaque coil, the thin outer tube commences. The signal transmitting cable extends from the sensor element to an electronic unit through an air channel within the thin outer tube.

U.S. Pat. No. 4,873,986 issued to Wallace, and entitled "Disposable Apparatus for Monitoring Intrauterine Pressure and Fetal Heart Rate," is directed to an apparatus to monitor the fetal condition during labor and childbirth. The apparatus includes a cable, a pressure transducer, a plug, and a pair of wires. The pressure transducer is located within the leading edge of the cable. The plug is located at a proximal end of the cable. The signals from the pressure transducer are conveyed to the plug by way of the pair of wires, which pass through a vent channel within the cable.

U.S. Pat. No. 6,428,489 issued to Jacobsen et al and entitled "Guidwire System," is directed to a catheter guidewire which includes an elongate solid body. Around this elongated solid body, a catheter is guided toward a target location in the vasculature system of a body. The elongate body includes a proximal end and a distal end, with the distal end being curved. Cuts are formed by either saw-cutting, laser cutting or etching at spaced-apart locations along the length of the body, thereby increasing the lateral flexibility of the guidewire. Integral beams are also formed within the body to maintain its torsional strength. The relative location and size of cuts and beams may be selectively adjusted, thereby determining the direction and degree of flexure, and the change in torsional stiffness relative to flexibility.

BRIEF SUMMARY OF THE INVENTION

The present invention is directed to a medical device, such as, for example, a guidewire. In an exemplary embodiment, the medical device, in accordance with the present teachings, comprises a corewire, a sensor core, and a coupler. The coupler has a first end and a second end. A portion of the corewire is disposed within the first end of the coupler, and a portion of the sensor core is disposed within the second end of the coupler. The coupler is operative to couple the corewire with the sensor core.

In another exemplary embodiment, the medical device comprises a corewire having a proximal end and a distal end, and a sensor assembly comprising a sensor core. The sensor core comprises a first end, a second end, and a bore in the first end. A portion of the corewire at the distal end thereof is disposed within the bore in the first end of the sensor core.

In accordance with another aspect of the invention, a method of manufacturing a medical device, such as, for example, a guidewire, is provided. In an exemplary embodiment, the method, in accordance with the present teachings, comprises the steps of providing a corewire, providing a sensor core configured to have a sensor mounted thereon, and providing a coupler configured to couple the corewire with the sensor core. The method further comprises inserting a portion of the corewire into a first end of the coupler. The method still further comprises inserting a portion of the sensor core into a second end of the coupler.

In another exemplary embodiment, the method comprises the steps of providing a sensor core configured to have a sensor mounted thereon and having a first end and a second end opposite the first end, and providing a corewire. The method further comprises the steps of forming a bore in the first end of the sensor core, and inserting a portion of the corewire into the bore.

The foregoing and other aspects, features, details, utilities, and advantages of the present invention will be apparent from reading the following description and claims, and from reviewing the accompanying drawings.

BRIEF DESCRIPTION OF THE DRAWINGS

FIG. 3B is an orthographic illustration, in top view, of the guidewire of FIG. 3A, constructed and operative in accordance with a further embodiment of the disclosed technique;

FIG. 3C is an orthographic illustration, in front view, of the guidewire of FIG. 3A, constructed and operative in accordance with another embodiment of the disclosed technique;

FIG. 9A is a schematic perspective exploded illustration of a guidewire constructed and operative in accordance with a further embodiment of the disclosed technique;

DETAILED DESCRIPTION OF EMBODIMENTS OF THE INVENTION

The disclosed technique overcomes the disadvantages of the prior art by providing a novel guidewire design and forming technique. The novel design enables electronic components, such as sensors and electrical wires, to be placed within the guidewire, in particular in the tip of the guidewire. Such electronic components allow for scalar and vector values to be measured at the guidewire's tip. The design also increases the flexibility of the guidewire, in particular at its distal end. The novel forming technique enables a guidewire to be formed having a substantially increased level of flexibility over prior art guidewires. Throughout the description, the guidewire of the disclosed technique is described in reference to medical guidewires. It is noted that the terms "position" and "location" are used interchangeably throughout the description and in general refer to the three dimension location of an object in a predefined coordinate system.

Figure 1A:
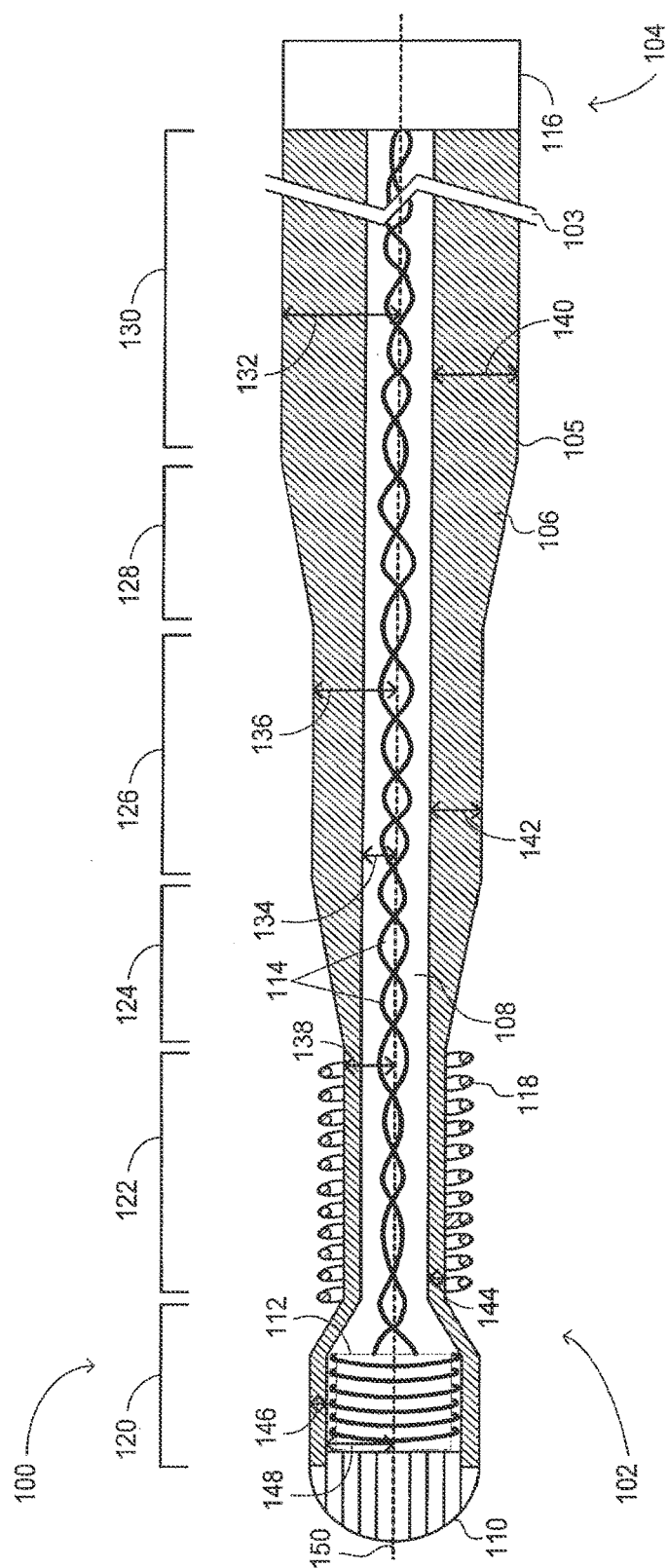
FIG. 1A is a schematic illustration of a guidewire in a cross-sectional view, constructed and operative in accordance with an embodiment of the disclosed technique.

Reference is now made to FIG. 1A, which is a schematic illustration of a guidewire, in a cross-sectional view, generally referenced 100, constructed and operative in accordance with an embodiment of the disclosed technique. FIG. 1A substantially shows the inside of guidewire 100. Guidewire 100 includes a hollow tube 105, a plug 110, a sensor 112, a twisted pair of wires 114 and a tubular spring 118. Guidewire 100 can be coupled with an interconnect 116. In general, guidewire 100 includes two sections, a distal section 102 and a proximal section 104. Distal section 102 refers to the distal end of guidewire 100, the end of guidewire 100 which is distant from interconnect 116. Proximal section 104 refers to the proximal end of guidewire 100, the end of guidewire 100 which is nearest to interconnect 116. In FIG. 1A, distal section 102 and proximal section 104 are separated by a set of lines 103. Hollow tube 105 includes a walled section 106 and a hollow section 108. Hollow section 108 can also be referred to as a cavity or a lumen. Twisted pair of wires 114, referred to herein as twisted pair 114, are coupled with sensor 112 and with interconnect 116. Plug 110 is coupled with the distal tip of guidewire 100. As explained in further detail below, tubular spring 118 is placed around a particular section of distal section 102 of guidewire 100. Sensor 112 and twisted pair of wires 114 are located inside hollow tube 105 in hollow section 108.

Sensor 112 is sensor capable of measuring scalar values such as pressure and temperature as well as vector values such as position and orientation of a magnetic field. For example, sensor 112 is a coil sensor capable of measuring the strength and orientation of a magnetic field. In general, micro-coil sensor can have a thickness on the order of a few hundred micrometers, such as 250 µm. Twisted pair 114 includes wires capable of transferring electrical signals from sensor 112 to interconnect 116. The wires of twisted pair 114 can have a thickness on the order of tens of micrometers, for example, between 10-25 µm. Plug 110 can be made of metal or of a polymer bonded into guidewire 100. Plug 110 may further be made of bonding material shaped into a hemispherical shape. Plug 110 is coupled to the distal tip of guidewire 100 by gluing, bonding, welding or soldering. Plug 110 can also just be glue. Tubular spring 118 is a tube exhibiting lateral flexibility (i.e., perpendicular to the central axis of the tube). Tubular spring 118 is, for example, a metal (e.g., stainless steel, platinum, iridium, nitinol) coil spring a flexible polymer tube or a braided or coiled plastic tube. Tubular spring 118 maintains the outer diameter of guidewire 100 over the length thereof (i.e., typically tubular spring 118 maintains diameter 132). Furthermore, tubular spring supports compressive loads and resists buckling of the section 122 without substantially increasing torsional and bending stiffness. Tubular spring 118 can also be made of a radiopaque material, which prevents radiation from passing there through. Interconnect 116 enables guidewire 100, and in particular twisted pair of wires 114, to be coupled with other devices, such as a computer, a power source, a device measuring magnetic field strength and orientation and the like. Guidewire 100 may be further covered by a thin elastic polymer layer (not shown) over sections 120 and 122. This polymer layer is typically a heat shrink tube of a few microns thickness, which provides a slick, smooth and lubricious surface.

As mentioned above, guidewire 100 can be used to measure various scalar and vector values and in particular scalar and vector values as detected and determined at the distal tip of guidewire 100. When sensor 112 is a micro-coil sensor, sensor 112 and located in the distal tip of guidewire 100, guidewire 100 can be used to determine the strength and orientation of a magnetic field at the distal tip of guidewire 100, which in turn can be used to determine the position and orientation of the distal tip of guidewire 100. For example, if guidewire 100 is used in a medical application, where guidewire 100 is inserted inside a living object, such as a human or an animal, then guidewire 100 can determine the position and orientation of its distal tip based on the measurements of sensor 112. In general, in such an application a magnetic field is generated in the vicinity of the living object and sensor 112 is capable of measuring the magnetic field strength and orientation. These measurements are provided as electrical signals from sensor 112 to twisted pair 114 which in turn provide the electrical signals to interconnect 116. Interconnect 116 can be coupled with a computer capable of determining the position and orientation of the micro-coil sensor based on the electrical signals received. Since sensor 112 is located in the distal tip of guidewire 100, the position and orientation of sensor 112 is substantially the position and orientation of the distal tip of guidewire 100.

In position sensing applications involving magnetic fields, magnetic interference, such as induced electrical currents, can cause errors and biases in the electrical signals provided from twisted pair 114 to interconnect 116. In order to reduce the amount of magnetic interference, the wires located inside hollow section 108 are generally twisted, which reduces the amount of induced electrical current in the wires due to the presence of a magnetic field. Furthermore, tubular spring 118 may be made of a radiopaque material such that it can be seen on an X-ray. If guidewire 100 is used in a medical application where it is inserted inside a living object, and tubular spring 118 is made of a radiopaque material, then, tubular spring 118 will appear on an X-ray of the living object and therefore, distal section 102 of the guidewire will also appear on the X-ray image. This information can be used along with the measurements of sensor 112 to enhance the determination of the position and orientation of the distal tip of guidewire 100.

Figure 1B:
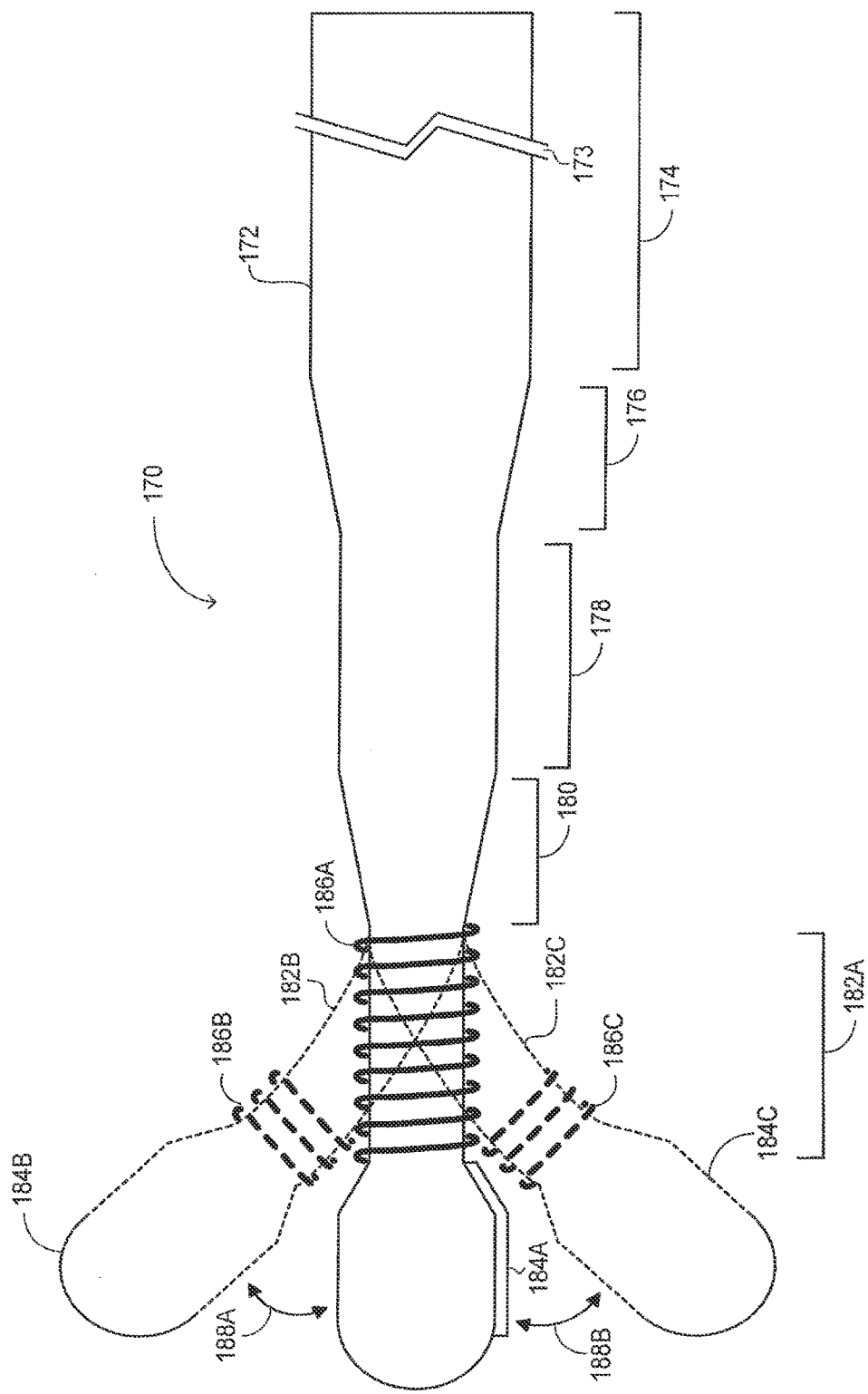
FIG. 1B is a schematic illustration showing the flexibility of a guidewire, constructed and operative in accordance with another embodiment of the disclosed technique.

As described in more detail in FIG. 1B, distal section 102 of guidewire 100 is flexible which provides increased maneuverability to guidewire 100. Increased maneuverability enables a user of guidewire 100 to more easily maneuver the guidewire when it is inserted into a living object. The flexibility of the distal end of guidewire 100 is achieved by changing the outer diameter of walled section 106 of hollow tube 105 as further described. In general, to increase the flexibility of hollow tube 105, it is required to reduce the outer diameter thereof, while maintaining the ability of hollow tube 105 to withstand compressive loads, buckling and kinking Hollow tube 105 is generally made of a metal, such as stainless steel or nitinol. In the embodiment shown in FIG. 1A, hollow tube 105 is made from a single piece of metal. The fact that hollow tube 105 is made of metal provides twisted pair 114 with shielding from electromagnetic interferences. Thus, twisted pair 114 may be an unshielded twisted pair, thereby reduce the thickness of twisted pair 114 to the order of tens of micrometers. Hollow tube 105 can be defined by the diameter of hollow section 108, known as the inner diameter, as well by the diameter of walled section 106, known as the outer diameter. In FIG. 1A, both the inner and outer diameters of hollow tube 105 are measured from a centerline 150. The inner diameter, as shown by an arrow 134, is substantially on the order of hundreds of micrometers, such as 100 µm. In cardio-logical applications, the inner, diameter shown by an arrow 134, is substantially on the order of tens of micrometers. As can be seen in FIG. 1A, the inner diameter of hollow tube 105 does not change along the length of guidewire 100. The outer diameter, as can be seen in FIG. 1A, changes along the length of guidewire 100, as shown by an arrow 132, an arrow 136 and an arrow 138. Hollow tube 105 can also be described in terms of the thickness of walled section 106. For example, as the outer diameter of hollow tube 105 reduces, the thickness of walled section 106 also reduces, as shown by an arrow 140, an arrow 142 and an arrow 144. The outer diameter shown by arrow 132 represents the original diameter of hollow tube 105, which is substantially on the order of hundreds of micrometers, such as 350 µm. In general, the outer diameter of distal section 102 of guidewire 100 is reduced, in a step-like, gradual manner, using various techniques such as grinding and drawing.

As can be seen in FIG. 1A, a first section 130 represents the shape of hollow tube 105 over a majority of the length of guidewire 100. Recall that lines 103 represent a break between the distal and proximal sections of guidewire 100 wherein the dimensions of the guidewire do not change and remain fixed. Guidewire 100 can measure, for example up to 200 centimeters. Section 130 can measure, for example, up to 160 centimeters. Adjacent to first section 130 is a first transition section 128, where the outer diameter of walled section 106 is gradually tapered until a first predetermined reduced outer diameter, such as the outer diameter defined by arrow 136. Adjacent to first transition section 128 is a second section 126, where the dimensions of the guidewire do not change and remain fixed. Adjacent to second section 126 is a second transition section 124, where the outer diameter of walled section 106 is gradually tapered until a second predetermined reduced outer diameter, such as the outer diameter defined by arrow 138. Adjacent to second transition section 124 is a third section, which is subdivided into a floppy section 122 and a sensor housing section 120. This third section is characterized in that the thickness of walled section 106 does not change and remains fixed as can be seen from arrow 144 and an arrow 146, both of which are the same size. In general, the length of the distal section, over which the diameter of the guidewire is reduced (i.e., sections 120, 122, 124, 126 and 128) is between 20-40 centimeters.

In general, the thickness of walled section 106 in the third section is substantially on the order of tens of micrometers, such as 25 µm, meaning that the outer diameter in floppy section 122, as shown by an arrow 138, is substantially on the order of hundreds of micrometers, such as 125 µm. At an outer diameter of hundreds of micrometers, floppy section 122 and sensor housing section 120 of guidewire 100 have increased flexibility and maneuverability. In general, floppy section 122 can typically measure between 40 mm to 300 mm. As floppy section 122 is flexible and not rigid, tubular spring 118 is placed around this section to strengthen the distal tip of guidewire 100 while at the same time not reducing its flexibility. Sensor housing section 120, which initially had an inner diameter similar to the inner diameter of floppy section 122, as shown by arrow 134, is enlarged to an inner diameter as shown by an arrow 148 such that sensor 112 can be inserted into sensor housing section 120. When sensor 112 is a micro-coil sensor, the thickness of sensor 112 may be on the order of hundreds of micrometers, such as 250 µm, meaning that the inner diameter of the distal tip of guidewire 100, in this example, is substantially doubled, from approximately 100 µm to 200 µm. The outer diameter of sensor housing section 120 can be increased by drawing the distal tip of guidewire 100 over a mandrel. In general, sensor housing section can typically measure between 1 mm and 5 mm. It is noted that the dimensions of the general configuration, as shown in FIG. 1A, can be changed and varied so as to provide increased flexibility, pushability, torque response and tactile feel. For example, more transitions sections or fewer transition sections could have been present in guidewire 100. The number of transition sections, as well as their respective length can be determined and altered by one skilled in the art according to the needs of a particular application, user or both. Alternatively, the outer diameter of guidewire 100 may decrease continuously, either linearly or according to a determined function (e.g., the outer diameter may decrease exponentially).

Reference is now made to FIG. 1B, which is a schematic illustration showing the flexibility of a guidewire, generally referenced 170, constructed and operative in accordance with another embodiment of the disclosed technique. Guidewire 170 is substantially similar to guidewire 100 (FIG. 1A). Guidewire 170 is constructed from a hollow tube 172. As in FIG. 1A, the distal and proximal sections of guidewire 170 are separated by a set of lines 173. As in FIG. 1A, hollow tube 172 is characterized by an outer diameter and an inner diameter, whereby the outer diameter of the hollow tube is reduced at the distal end of the guidewire. Guidewire 170 includes a first section 174, which represents the shape of hollow tube 172 over a majority of the length of guidewire 170. In first section 174, the dimensions of the guidewire do not change and remain fixed. Adjacent to first section 174 is a first transition section 176, where the outer diameter of hollow tube 172 is gradually tapered until a first predetermined reduced outer diameter. Adjacent to first transition section 176 is a second section 178, where the dimensions of the guidewire do not change and remain fixed. Adjacent to second section 178 is a second transition section 180, where the outer diameter of hollow tube 172 is gradually tapered until a second predetermined reduced outer diameter. Adjacent to second transition section 172 is a third section, which is subdivided into a floppy section 182A and a sensor housing section 184A. This third section is characterized in that the thickness of the walled section of hollow tube 172 (not shown) does not change and remains fixed.

In FIG. 1B, a tubular spring 186A is placed around floppy section 182A in order to strengthen the third section while also maintaining the flexibility of this section. Two additional positions of the floppy section and the sensor housing section of guidewire 170 are shown using broken lines, demonstrating the flexible nature of the third section. In a first additional position, shown by a floppy section 182B, a sensor housing section 184B and a tubular spring 186B, the distal end of guidewire 170 is displaced by an amount shown as an arrow 188A. In a second additional position, shown by a floppy section 182C, a sensor housing section 184C and a tubular spring 186C, the distal end of guidewire 170 is displaced by an amount shown as an arrow 188B. Due reduced outer diameter of the floppy section and the sensor housing section of guidewire 170, the two additional positions shown in FIG. 1B are possible. Also, because the tubular spring applies a restoring force when the distal end of guidewire 170 is in either of the two additional positions shown in FIG. 1B, the distal end of guidewire 170 maintains a certain amount of rigidness as the tubular spring is always trying to maintain the floppy section in the position of floppy section 182A.

Figure 2:
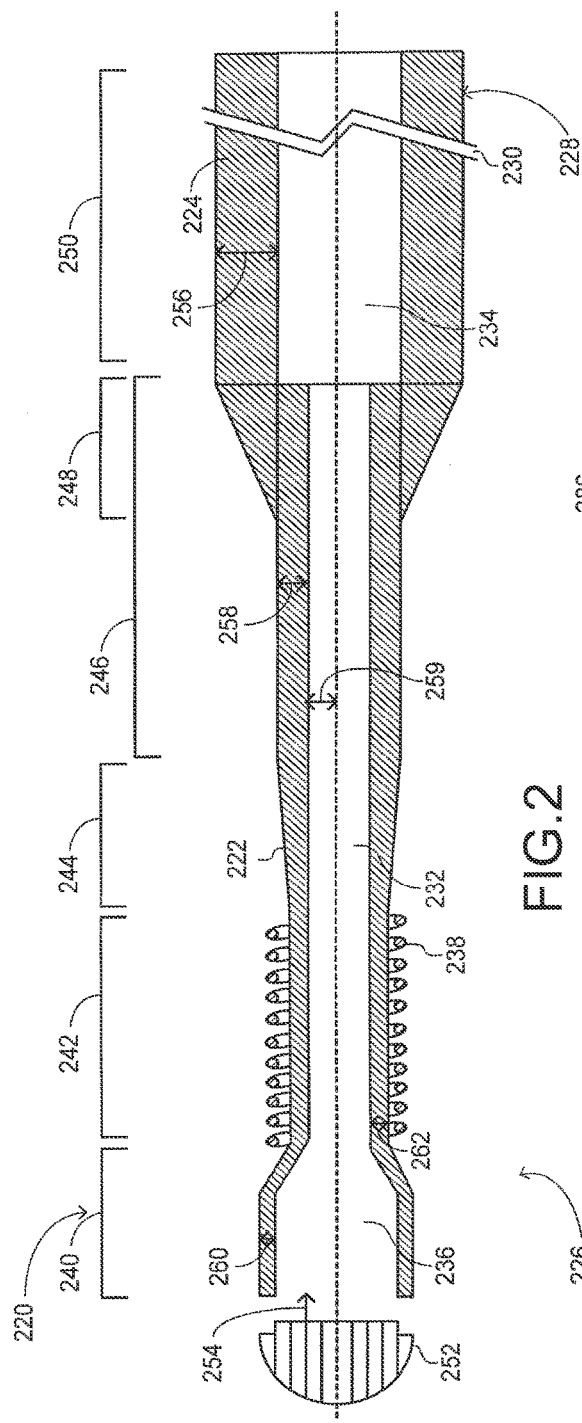
FIG. 2 is a schematic illustration of another guidewire, in a cross-sectional view, constructed and operative in accordance with a further embodiment of the disclosed technique.

Reference is now made to FIG. 2, which is a schematic illustration of another guidewire, in a cross-sectional view, generally referenced 220, constructed and operative in accordance with a further embodiment of the disclosed technique. Guidewire 220 is substantially similar to guidewire 100 (FIG. 1A) and includes a distal section 226, a proximal section 228 and a set of lines 230 separating the two. Unlike the embodiment of the guidewire shown in FIG. 1A, guidewire 220 is constructed from two hollow tubes of different inner and outer diameters, a thicker hollow tube 224 and a thinner hollow tube 222. Thicker hollow tube 224 and thinner hollow tube 222 can both be hypotubes. In general, thinner hollow tube 222 is shorter in length than thicker hollow tube 224. For example, thinner hollow tube 222 may typically measure between 5 and 30 centimeters, whereas thicker hollow tube 224 may typically measure between 160 and 170 centimeters. As in FIG. 1A, guidewire 220 includes a tubular spring 238 and a plug 252, which is placed over the distal end of guidewire 220 in the direction of an arrow 254. Guidewire 220 has a lumen 236, where a sensor (not shown) can be placed, and a hollow section 232, where a twisted pair of wires (not shown) can be placed, which are coupled with the sensor. Guidewire 220 can also be coupled with an interconnect (not shown). Similar to guidewire 100 (FIG. 1A), guidewire 220 may be also be covered by a thin elastic polymer layer (not shown) over sections 240 and 242.

As in FIG. 1A, guidewire 220 has an initial outer diameter which is tapered in distal section 226 to enable the distal section of guidewire 220 to have increased flexibility. As shown in FIG. 2, guidewire 220 includes a first section 250, which represents the shape of thicker hollow tube 224 over a majority of the length of guidewire 220. In first section 250, the dimensions of the guidewire do not change and remain fixed. Adjacent to first section 250 is a first transition section 248, where the outer diameter of thicker hollow tube 224 is gradually tapered until a first predetermined reduced outer diameter. Adjacent to first transition section 248 and partially overlapping is a second section 246, where the dimensions of the guidewire do not change and remain fixed. The second section represents the initial shape of thinner hollow tube 222. Adjacent to second section 246 is a second transition section 244, where the outer diameter of thinner hollow tube 222 is gradually tapered until a second predetermined reduced outer diameter. Adjacent to second transition section 244 is a third section, which is subdivided into a floppy section 242 and a sensor housing section 240. This third section is characterized in that the thickness of the walled section of thinner hollow tube 222 does not change and remains fixed as shown by arrows 260 and 262.

In general, the outer and inner diameters of both thicker hollow tube 224 and thinner hollow tube 222 are on the order of hundreds of micrometers. For example, the inner and outer diameters of thicker hollow tube 224 may respectfully be 180 μm and 350 μm, whereas the inner and outer diameters of thinner hollow tube 222 may respectfully be 100 μm and 180 μm. The inner diameter of thinner hollow tube 222 is shown as an arrow 259. In general, the outer diameter of the thinner hollow tube is selected such that it is substantially similar to the inner diameter of the thicker hollow tube. In the embodiment shown in FIG. 2, thicker hollow tube 224 is coupled with thinner hollow tube 222 by either welding, bonding or gluing. As shown in FIG. 2, the area which is coupled between the two hollow tubes is where first transition section 248 and second section 246 overlap.

In this embodiment, the initial thickness of the walled section of each hollow tube, as shown by an arrow 256 and an arrow 258, is reduced and tapered by reducing the outer diameter of the walled section of each hollow tube. As mentioned above, the outer diameter can be reduced by grinding or drawing. In one embodiment, the outer diameters of thicker hollow tube 224 and thinner hollow tube 222 are both reduced after they have been coupled together. In another embodiment, the outer diameters of thicker hollow tube 224 and thinner hollow tube 222 are both reduced before they are coupled together. In a further embodiment, the outer diameters of thicker hollow tube 224 and thinner hollow tube 222 are both reduced before they are coupled together and after they are coupled together. It is noted that in this embodiment, sensor housing section 240 can be formed (i.e., the distal end of guidewire 220 can be enlarged) before tubular spring 238 is placed on floppy section 242. This can be achieved by first enlarging the distal end of guidewire 220 before thicker hollow tube 224 and thinner hollow tube 222 are coupled together. Once the distal end has been enlarged, tubular spring 238 can be placed over floppy section 242 and then thicker hollow tube 224 and thinner hollow tube 222 can be coupled together, thereby trapping tubular spring 238 between the larger outer diameters of sensor housing section 240 and first section 250. In another embodiment, the two hollow tubes can first be coupled together, then tubular spring 238 can be placed over floppy section 242 and finally, sensor housing section 240 can be enlarged to fit the sensor. As mentioned above in conjunction with FIG. 1A, the dimensions of the general configuration, as shown in FIG. 2, can be changed and varied so as to provide increased flexibility, pushability, torque response and tactile feel. For example, more transitions sections could have been present in guidewire 220. The number of transition sections, as well as their respective length can be determined and altered by one skilled in the art according to the needs of a particular application, user or both.

Figure 3A:
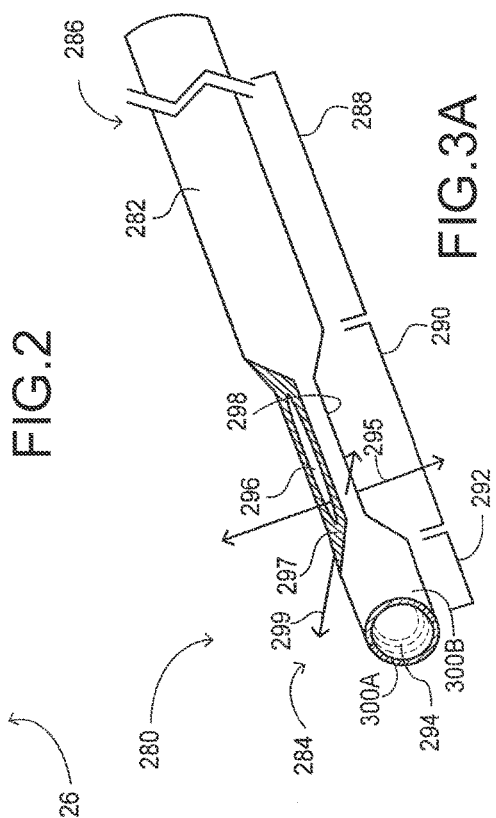
FIG. 3A is a perspective illustration of a guidewire having a tip which exhibits substantially increased flexibility, constructed and operative in accordance with another embodiment of the disclosed technique.

Reference is now made to FIG. 3A, which is a perspective illustration of a guidewire having a tip which exhibits substantially increased flexibility, generally referenced 280, constructed and operative in accordance with another embodiment of the disclosed technique. In general, the flexibility of the hollow tubes illustrated in FIGS. 1A and 2 are determined by the thickness of the walled section of each guidewire near the distal end, as shown by arrows 144 (FIG. 1A) and 146 (FIG. 1A) for guidewire 100 (FIG. 1A), and as shown by arrows 260 (FIG. 2) and 262 (FIG. 2) for guidewire 220 (FIG. 2). The flexibility is also determined by the inner diameter of each guidewire, as shown by arrow 134 (FIG. 1A) for guidewire 100 and by arrow 259 for guidewire 220. By reducing the thickness of the walled sections of these guidewires near the distal end and by reducing the inner diameter, the flexibility of these guidewires can be increased. This flexibility is limited by two factors, the first being the minimal size of the inner diameter of each guidewire such that a twisted pair of wires can be threaded through. The second is the minimal thickness of the walled section of each guidewire such that the general form of the guidewire is maintained and that the walled section of each guidewire does not break or tear during use. In FIG. 3A, the distal end of guidewire 280 is formed, according to the disclosed technique, in a manner such that it exhibits increased flexibility over the flexibility of guidewires 100 and 220. Thus the distal tip of guidewire 280 exhibits substantial maneuverability.

Guidewire 280 is substantially similar to guidewire 100. Guidewire 280 has a distal section 284 and a proximal section 286. Guidewire 280 is constructed from a hollow tube 282. Guidewire 280 can be coupled with an interconnect (not shown). Also, guidewire 280 has a sensor (not shown) and a twisted pair of wires (not shown) threaded through the lumen (not shown) of hollow tube 282. The outer diameter of guidewire 280 is tapered in distal section 284 and the distal end of guidewire 280 is enlarged to enable the sensor to be placed therein. As in guidewire 100, the inner diameter of hollow tube 282 remains constant along the length of the guidewire. Guidewire 280 has a first section 288, where the outer diameter of the guidewire remains fixed and constant along a majority of the length of the guidewire. Adjacent to first section 288 is a floppy section 290, where the outer diameter of guidewire 280 is reduced to a predetermined reduced outer diameter and then kept constant at the predetermined reduced outer diameter. A tubular spring (not shown) can be placed around floppy section 290. Adjacent to floppy section 290 is a sensor housing section 292 where the sensor is placed. As can be seen in FIG. 3A, sensor housing section 292 is enlarged to enable the sensor to fit in. Similar to guidewire 100 (FIG. 1A), guidewire 280 may be also be covered by a thin elastic polymer layer (not shown) over sections 290 and 292.

In guidewire 280, a part of the walled section of hollow tube 282, in floppy section 290, is completely removed, thereby exposing the lumen of hollow tube 282. This is illustrated in FIG. 3A as an opening 296 and an opening 298. Openings 296 and 298 are located at opposite sides of hollow tube 282, thereby increasing the flexibility of guidewire 280 in a horizontal plane, as shown by an arrow 299. An area 297 represents the walled section of hollow tube 282 which is visible once a part of the walled section in floppy section 290 has been removed. The walled section removed in floppy section 290 can be removed by either grinding or cutting by laser. Besides removing a part of the walled section in floppy section 290, hollow tube 282 is split in two in a vertical plane, as shown by an arrow 295, from the beginning of sensor housing section 292 to substantially the end of floppy section 290. This splitting generates two distal ends (i.e., two prongs) in distal section 284, a distal end 300A and a distal end 300B. This is more clearly illustrated in FIG. 3B. It is noted that other embodiments of the construction of distal section 284 are possible. For example, instead of removing the upper and lower sides of the walled section of floppy section 290, the lateral sides of the walled section of floppy section 290 can be removed. In this embodiment, the sensor housing section and the floppy section would be split into two in a horizontal plane.

Once distal section 284 has been constructed as shown in FIG. 3A, the sensor is placed inside an opening 294, and the twisted wire pair, coupled with the sensor, are threaded through the lumen of hollow tube 282. Openings 296 and 298 may be filled with a glue to prevent the twisted pair of wires from moving and being exposed. However, when the glue affects the flexibility of distal section 284, glue may be applied only at selected locations along distal section 284 to prevent the twisted pair of wires from moving. Also distal ends 300A and 300B can be glued to the sensor to keep the sensor in place. A plug (not shown) can be placed over opening 294 to seal the sensor in. Similar to guidewire 100 (FIG. 1A), guidewire 320 may be also be covered by a thin elastic polymer layer (not shown) over sections 290 and 292.

Reference is now made to FIG. 3B, which is an orthographic illustration, in top view, of the guidewire of FIG. 3A, generally referenced 320, constructed and operative in accordance with a further embodiment of the disclosed technique. As can be seen in FIG. 3B, guidewire 320 is constructed from hollow tube 322, which is substantially similar to hollow tube 282 (FIG. 3A). Guidewire 320 has a proximal section 324 and a distal section 326 as well as a first section 332, a floppy section 330 and a sensor housing section 328. First section 332, floppy section 330 and sensor housing section 328 are respectively substantially similar to first section 288 (FIG. 3A), floppy section 290 (FIG. 3A) and sensor housing section 292 (FIG. 3A). As can be seen from the top view of FIG. 3B, sensor housing section 328 and floppy section 330 are split into two distal ends, a distal end 336A and a distal end 336B. A hollow 334 is where a sensor (not shown) is placed, in between distal end 336A and 336B.

Reference is now made to FIG. 3C, which is an orthographic illustration, in front view, of the guidewire of FIG. 3A, also showing cross-sections of the guidewire, generally referenced 350, constructed and operative in accordance with another embodiment of the disclosed technique. As can be seen in FIG. 3C, guidewire 350 is substantially similar to guidewire 280. Guidewire 350 has a proximal section 354 and a distal section 356 as well as a first section 366, a first transition section 364, a floppy section 362, a second transition section 360 and a sensor housing section 358. First section 366, floppy section 362 and sensor housing section 358 are respectively substantially similar to first section 288 (FIG. 3A), floppy section 290 (FIG. 3A) and sensor housing section 292 (FIG. 3A). A first transition section and a second transition section are shown in both FIGS. 3A and 3B but are not specifically numbered.

In FIG. 3C, dash-dot lines $368_1$, $368_2$, $368_3$, $368_4$ and $368_5$ represent cut-away cross-sections of guidewire 350. In first section 366, a cross-section 370 shows that the hollow tube forming guidewire 350 has an initial outer diameter and is completely closed. In first transition section 364, the cross-sections 372A and 372B show that the outer diameter has been reduced and that the hollow tube of the guidewire is not completely closed and is split into two sections. As can be seen, the outer diameter of cross-sections 372A and 372B is smaller than the outer diameter of cross-section 370. It should be noted that in first transition section 364, a minority amount of the walled section of the hollow tube has been completely removed, as this represents the beginning of the area of guidewire 350 where the walled section of the hollow tube is removed. In floppy section 362, the cross-sections 374A and 374B show that the outer diameter has been further reduced from that of cross-sections 372A and 372B, and that the majority of the walled section of the hollow tube of the guidewire has been completely removed. In second transition section 360, the cross-sections 376A and 376B show that the outer diameter now remains constant, as the outer diameter of these cross-sections is substantially similar to the outer diameter as shown in cross-sections 374A and 374B. These cross-sections also show that only a minority of the walled section of the hollow tube of the guidewire has been completely removed, as this represents the end of the area of guidewire 350 where the walled section of the hollow tube is removed. In sensor housing section 358, the cross-sections 378A and 378B show that the outer diameter is still constant, as the outer diameter of these cross-sections is substantially similar to the outer diameter as shown in cross-sections 374A, 374B, 376A and 376B. Also, these cross-sections show that the hollow tube is cut in a vertical plane and split into two sections which are not coupled (i.e., two prongs).

Figure 4:
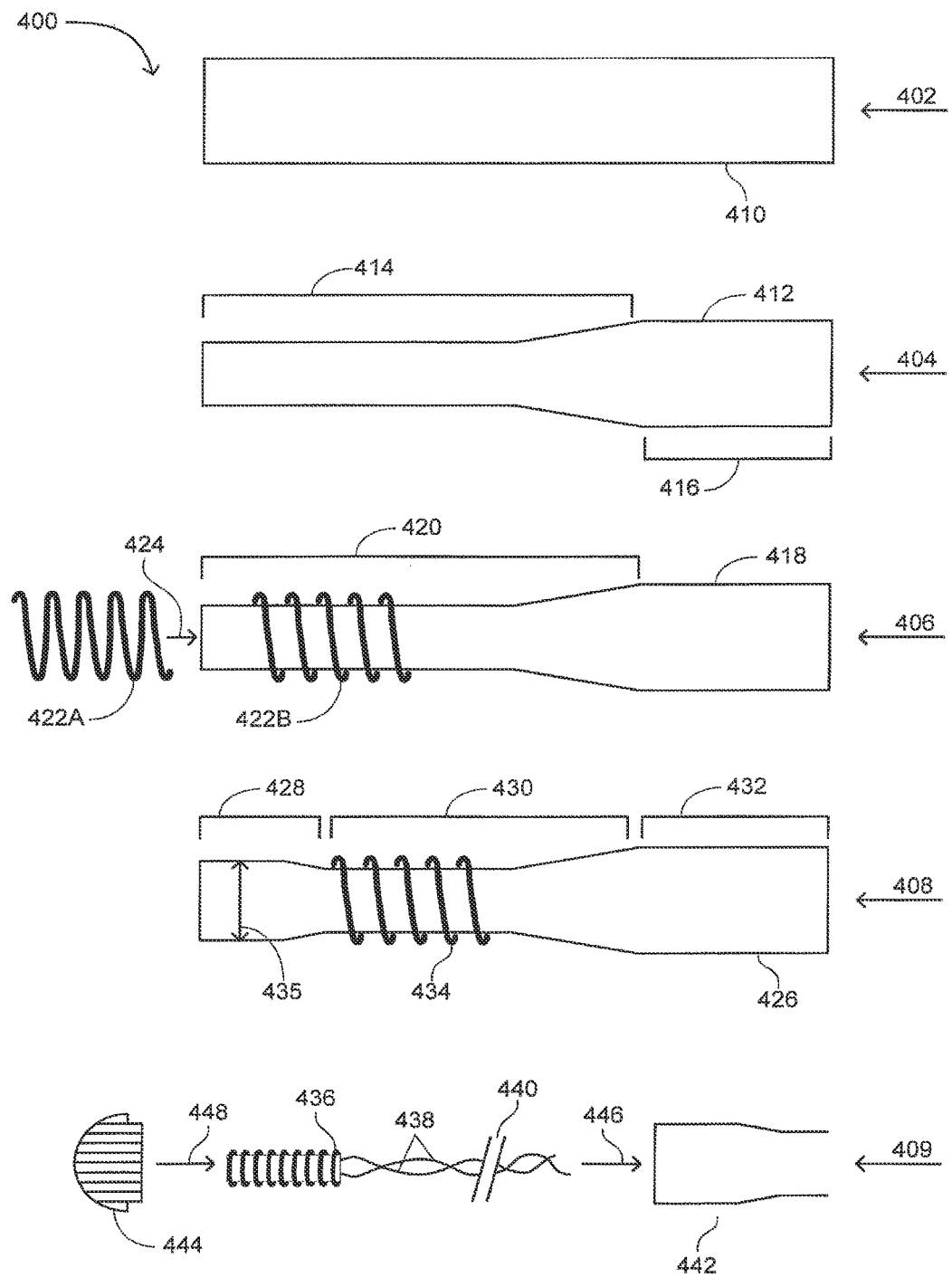
FIG. 4 is a schematic illustration showing the procedures executed in forming the guidewire of FIG. 3A, constructed and operative in accordance with a further embodiment of the disclosed technique.

Reference is now made to FIG. 4, which is a schematic illustration showing the procedures executed in forming the guidewire of FIG. 3A, generally referenced 400, constructed and operative in accordance with a further embodiment of the disclosed technique. In a first procedure 402, a hollow tube 410 having a fixed inner and outer diameter is selected. In a second procedure 404, the outer diameter of a distal section 414 of a hollow tube 412 is reduced in a step-like, gradual manner. The outer diameter of a proximal section 416 of hollow tube 412 remains constant. As mentioned above, the outer diameter can be reduced by grinding or by drawing. In procedure 404, a sub-section 415 of distal section 414 may be further grounded, or cut by a laser, to completely remove a part of the walled section of hollow tube 412 in sub-section 415, as shown as openings 296 and 298 (both in FIG. 3A) in FIG. 3A. Also, in procedure 404, distal section 414 is cut all the way through in a vertical plane, thereby generating two distal ends (not shown).

In a third procedure 406, once the outer diameter of a distal section 420 has been reduced and distal section 420 of a hollow tube 418 has been split into two, a tubular spring 422A such as a coil spring is placed over distal section 420 in the direction of an arrow 424. The tubular spring is placed over distal section 420 until it is in the location of a tubular spring 422B. In a fourth procedure 408, the distal end of a hollow tube 426 is enlarged, for example, by of drawing or pulling hollow tube 426 over a mandrel, or stamping the tip over a mandrel between two die sections thereby generating a sensor housing section 428. Section 428 may further be reinforced by a small section of thin tube placed there over there by holding the split section. A tubular spring 434 is essentially trapped in a floppy section 430, as the diameters of a first section 432 and sensor housing section 428 are larger than the diameter of tubular spring 434. The diameter of sensor housing section 428, as shown by an arrow 435, which represents the full diameter of sensor housing section 428 and not the inner or outer diameter of that section, is large enough that a tubular spring (not shown) can be inserted. In a fifth procedure 409, once the general configuration of the guidewire has been prepared, a sensor 436, coupled with a twisted pair of wires 438, referred herein as twisted pair 438, are threaded into the guidewire, in the direction of an arrow 446, through a sensor housing section 442. It is noted that twisted pair 438 may be long, as represented by set of lines 440. Once sensor 436 and twisted pair 438 are threaded through the guidewire, a plug 444 is inserted over the opening of sensor housing section 442 in the direction of an arrow 448. As mentioned above, a sensor 436 may be glued or bonded to the inner sides of sensor housing section 442. Also, the floppy section (not shown) of the guidewire may be covered with a glue to cover any section of twisted pair of wires 438 which are exposed. Twisted pair 438 can then be coupled with an interconnect, thereby generating a finished, functional guidewire, substantially similar in configuration to guidewire 280 (FIG. 3A) and in functionality to guidewire 100 (FIG. 1A). Additionally, an elastic polymer layer may be applied to the distal end of the guidewire. This elastic polymer layer is typically a heat shrink tube having a thickness in the order of a few microns, which provides a slick, smooth, lubricious surface.

Figure 5A:
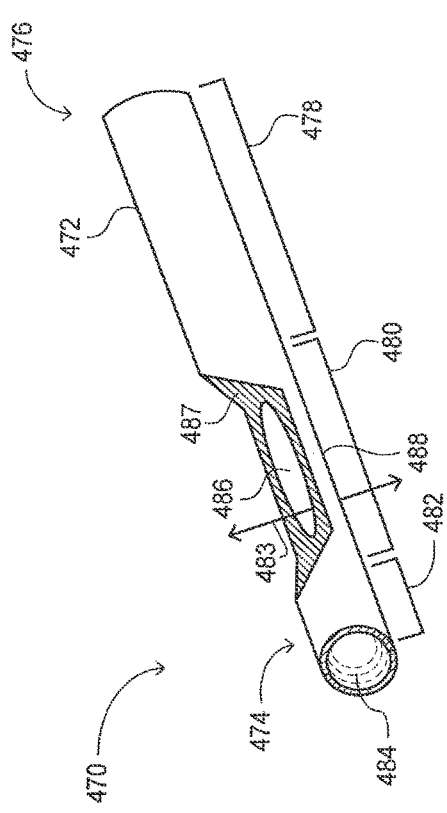
FIG. 5A is a perspective illustration of another guidewire having a substantially flexible tip, constructed and operative in accordance with another embodiment of the disclosed technique.

Reference is now made to FIG. 5A, which is a perspective illustration of another guidewire having a substantially flexible tip, generally referenced 470, constructed and operative in accordance with another embodiment of the disclosed technique. In FIG. 5A, the distal end of guidewire 470 is formed, according to the disclosed technique, in a manner such that it exhibits increased flexibility over the flexibility of guidewires 100 (FIG. 1A) and 220 (FIG. 2). Thus, the distal tip of guidewire 470 exhibits substantial flexibility, similar to the flexibility of guidewire 280 (FIG. 3A). Guidewire 470 is substantially similar to guidewire 100. Guidewire 470 has a distal section 474 and a proximal section 476. Guidewire 470 is constructed from a hollow tube 472. Guidewire 470 can be coupled with an interconnect (not shown). Also, guidewire 470 has a sensor (not shown) and a twisted pair of wires (not shown) threaded through the lumen (not shown) of hollow tube 472. The outer diameter of guidewire 470 is tapered in distal section 474 and the distal end of guidewire 470 is enlarged to enable the sensor to be placed therein. As in guidewire 100, the inner diameter of hollow tube 472 remains constant along the length of the guidewire. Guidewire 470 has a first section 478, where the outer diameter of the guidewire remains fixed and constant along a majority of the length of the guidewire. Adjacent to first section 478 is a floppy section 480, where the outer diameter of guidewire 470 is reduced to a predetermined reduced outer diameter and then kept constant at the predetermined reduced outer diameter. A tubular spring (not shown) can be placed around floppy section 480. Adjacent to floppy section 480 is a sensor housing section 482 where the sensor is placed. As can be seen in FIG. 5A, sensor housing section 482 is enlarged to enable the sensor to fit in. Similar to guidewire 100 (FIG. 1A), guidewire 470 may be also be covered by a thin elastic polymer layer (not shown) over sections 488 and 488.

In guidewire 470, a part of the walled section of hollow tube 472, in floppy section 480, is completely removed, thereby exposing the lumen of hollow tube 472. This is illustrated in FIG. 5A as an opening 486. As opposed to the configuration of guidewire 280 (FIG. 3A), guidewire 470 has an opening on only one side of hollow tube 472. Opening 486 is located on the upper side of hollow tube 472, thereby giving guidewire 470 an increase in flexibility in a vertical plane, as shown by an arrow 483. An area 487 represents the walled section of hollow tube 472 which is visible once a part of the walled section in floppy section 480 has been removed. The walled section removed in floppy section 480 can be removed by either grinding or cutting by laser. Unlike the configuration in FIG. 3A, floppy section 480 and sensor housing section 482 are not split into two separate ends. It is noted that other embodiments of the construction of distal section 474 are possible. For example, instead of removing the upper side of the walled section of floppy section 480, the lateral side or the lower side of the walled section of floppy section 480 can be removed. Once distal section 474 has been constructed as shown in FIG. 5A, the sensor is placed inside an opening 484, and the twisted pair of wires coupled with the sensor are threaded through the lumen of hollow tube 472. Opening 486 can be filled with a glue to prevent the twisted pair of wires from being exposed. A plug (not shown) can be placed over opening 484 to seal in the sensor.

Figure 5B:
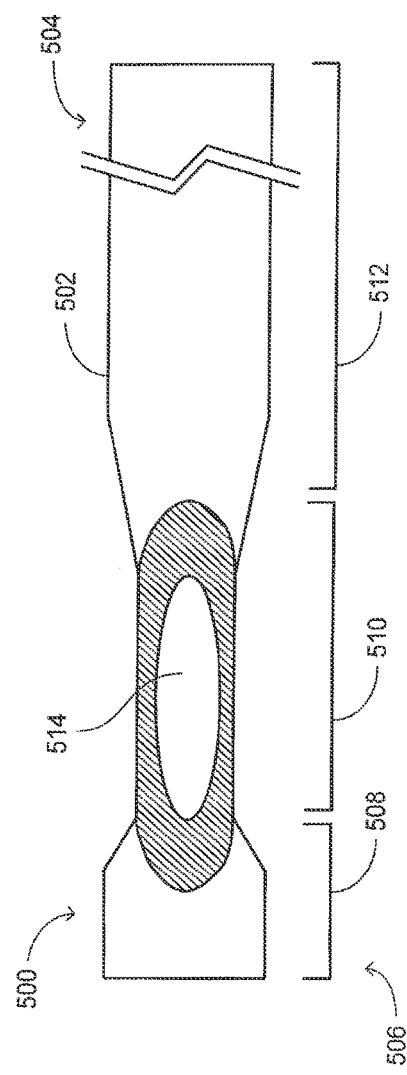
FIG. 5B is an orthographic illustration, in top view, of the guidewire of FIG. 5A, constructed and operative in accordance with a further embodiment of the disclosed technique.

Reference is now made to FIG. 5B, which is an orthographic illustration, in top view, of the guidewire of FIG. 5A, generally referenced 500, constructed and operative in accordance with a further embodiment of the disclosed technique. As can be seen in FIG. 5B, guidewire 500 is constructed from hollow tube 502, which is substantially similar to hollow tube 472 (FIG. 5A). Guidewire 500 has a proximal section 504 and a distal section 506 as well as a first section 512, a floppy section 510 and a sensor housing section 508. First section 512, floppy section 510 and sensor housing section 508 are respectively substantially similar to first section 478 (FIG. 5A), floppy section 480 (FIG. 5A) and sensor housing section 482 (FIG. 5A). As can be seen from the top view of FIG. 5B, a part of the walled section of floppy section 510 is completely removed. Unlike the guidewire shown in FIG. 3B, sensor housing section 508 is not split into two distal ends. Similar to guidewire 100 (FIG. 1A), guidewire 470 may be also be covered by a thin elastic polymer layer (not shown) over sections 508 and 510.

Figure 5C:
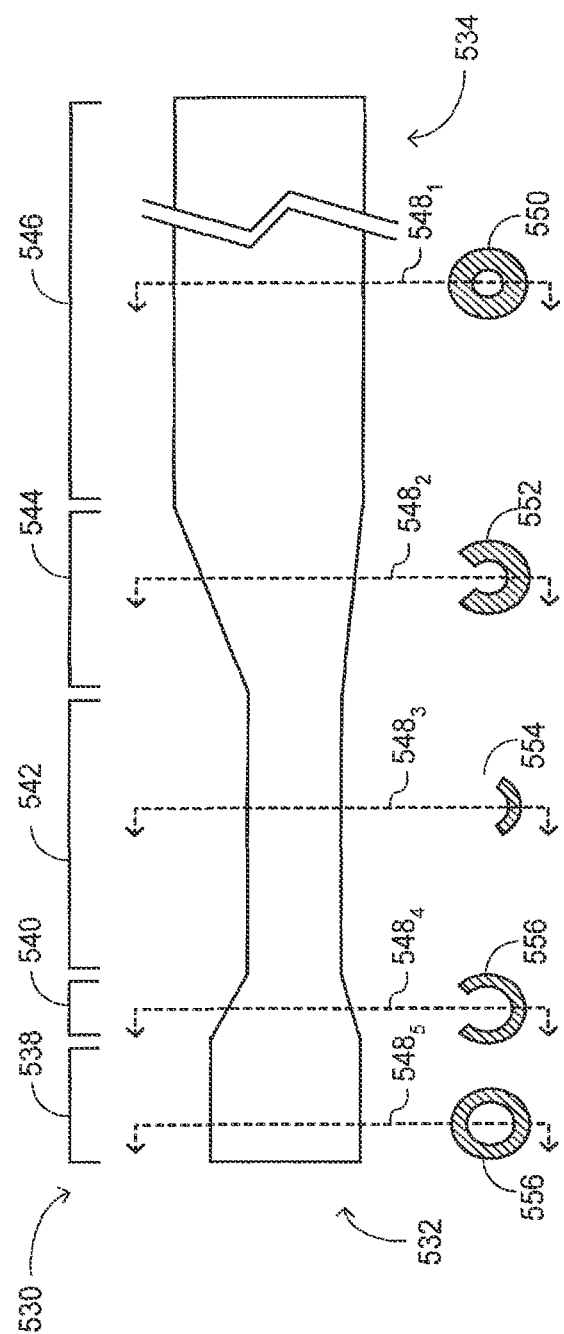
FIG. 5C is an orthographic illustration, in front view, of the guidewire of FIG. 5A, also showing cross-sections of the guidewire, constructed and operative in accordance with another embodiment of the disclosed technique.

Reference is now made to FIG. 5C, which is an orthographic illustration, in front view, of the guidewire of FIG. 5A, also showing cross-sections of the guidewire, generally referenced 530, constructed and operative in accordance with another embodiment of the disclosed technique. As can be seen in FIG. 5C, guidewire 530 is substantially similar to guidewire 470. Guidewire 530 has a proximal section 534 and a distal section 532 as well as a first section 546, a first transition section 544, a floppy section 542, a second transition section 540 and a sensor housing section 538. First section 546, floppy section 542 and sensor housing section 538 are respectively substantially similar to first section 478 (FIG. 5A), floppy section 480 (FIG. 5A) and sensor housing section 482 (FIG. 5A). A first transition section and a second transition section are shown in both FIGS. 5A and 5B but are not specifically numbered.

In FIG. 5C, dash-dot lines $548_1$, $548_2$, $548_3$, $548_4$ and $548_5$ represent cut-away cross-sections of guidewire 530. In first section 546, a cross-section 550 shows that the hollow tube forming guidewire 530 has an initial outer diameter and is completely closed. In first transition section 544, the cross-section 552 shows that the outer diameter has been reduced and that the hollow tube of the guidewire is not completely closed. As can be seen, the outer diameter of cross-section 552 is smaller than the outer diameter of cross-section 550. It should be noted that in first transition section 544, a minority amount of the walled section of the hollow tube has been completely removed, as this represents the beginning of the area of guidewire 530 where the walled section of the hollow tube is removed. In floppy section 542, the cross-section 554 shows that the outer diameter has been further reduced from that of cross-section 552, and that the majority of the walled section of the hollow tube of the guidewire has been completely removed thereby creating a single prong. In second transition section 540, the cross-section 556 shows that the outer diameter now remains constant, as the outer diameter of this cross-section is substantially similar to the outer diameter as shown in cross-section 554. This cross-section also show that only a minority of the walled section of the hollow tube of the guidewire has been completely removed, as this represents the end of the area of guidewire 530 where the walled section of the hollow tube is removed. In sensor housing section 538, the cross-section 558 shows that the outer diameter is still constant, as the outer diameter of this cross-section is substantially similar to the outer diameter as shown in cross-sections 556 and 554. Also, this cross-section shows that the hollow tube is completed, as in cross-section 550.

Figure 6:
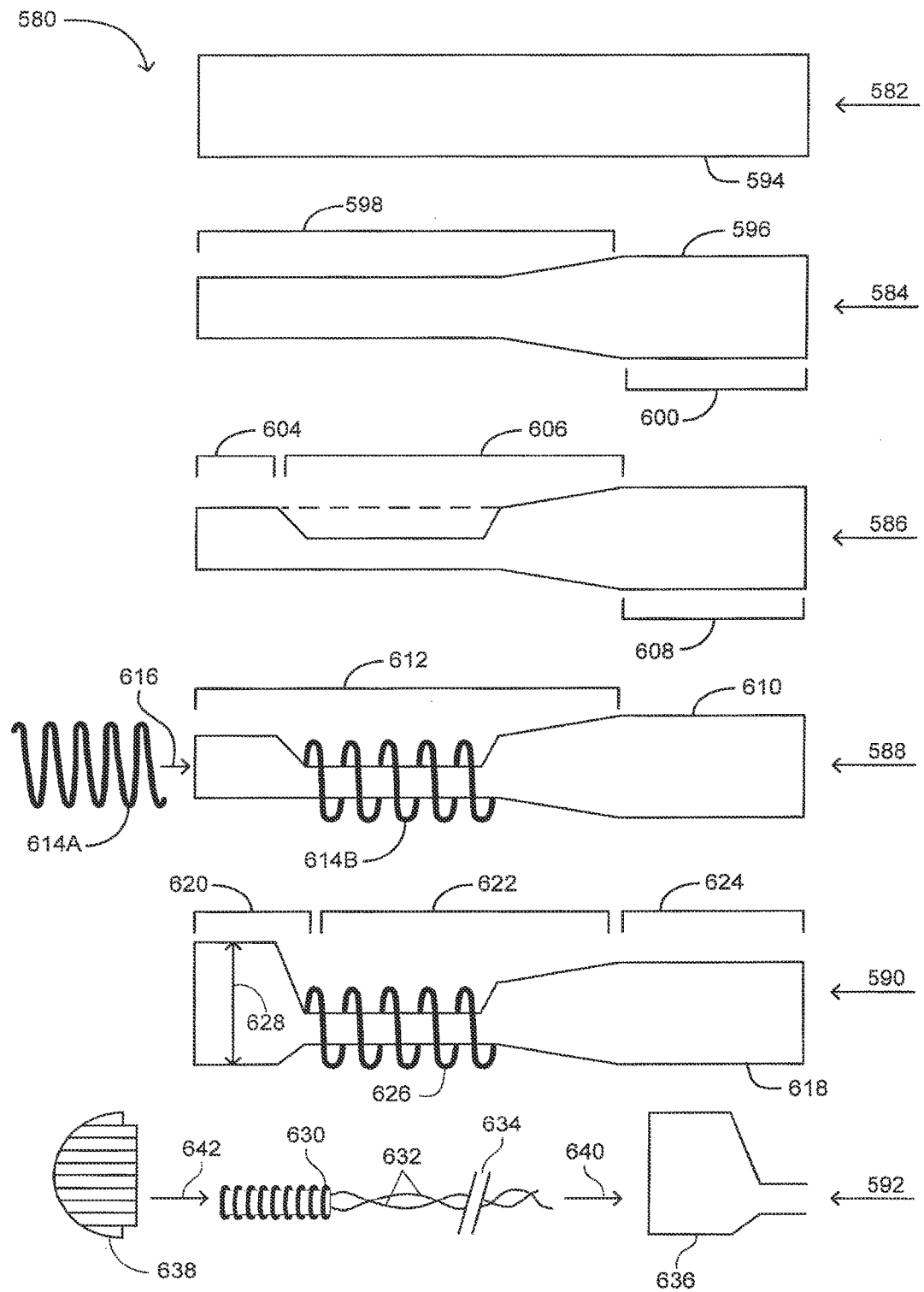
FIG. 6 is a schematic illustration showing the procedures executed in forming the guidewire of FIG. 5A, constructed and operative in accordance with a further embodiment of the disclosed technique.

Reference is now made to FIG. 6, which is a schematic illustration showing the procedures executed in forming the guidewire of FIG. 5A, generally referenced 580, constructed and operative in accordance with a further embodiment of the disclosed technique. In a first procedure 582, a hollow tube 594 having a fixed inner and outer diameter is selected. In a second procedure 584, the outer diameter of a distal section 598 of a hollow tube 596 is reduced in a step-like, gradual manner. The outer diameter of a proximal section 600 of hollow tube 596 remains constant. As mentioned above, the outer diameter can be reduced by grinding or by drawing. In a third procedure 586, a sub-section 606 of the distal section may be further grounded, or cut by a laser, to completely remove a part of the walled section of a hollow tube 602 in sub-section 606, as shown as opening 486 (FIG. 5A) in FIG. 5A. The area of the distal section cut out to generate sub-section 606 is shown as a dotted line in procedure 586. As can be seen, the diameter of sub-section 606 is smaller than the diameter of another sub-section 604.

In a fourth procedure 588, once the outer diameter of a distal section 612 has been reduced, a tubular spring 614A is placed over distal section 612 in the direction of an arrow 616. The tubular spring is placed over distal section 612 until it is in the location of a tubular spring 614B. In a fifth procedure 590, the distal end of a hollow tube 618 is enlarged, thereby generating a sensor housing section 620. A tubular spring 626 is essentially trapped in a floppy section 622, as the diameters of a first section 624 and sensor housing section 620 are larger than the diameter of tubular spring 626. The diameter of sensor housing section 620, as shown by an arrow 628, which represents the full diameter of sensor housing section 620 and not the inner or outer diameter of that section, is large enough that a tubular spring (not shown) can be inserted. In a sixth procedure 592, once the general configuration of the guidewire has been prepared, a sensor 630, coupled with a twisted pair of wires 632, referred to herein as twisted pair 632, are threaded into the guidewire, in the direction of an arrow 640, through a sensor housing section 636. It is noted that twisted pair 632 may be long, as represented by set of lines 634. Once sensor 630 and twisted pair 632 are threaded through the guidewire, a plug 638 is inserted over the opening of sensor housing section 636 in the direction of an arrow 642. As mentioned above, the floppy section (not shown) of the guidewire may be covered with a glue to cover any section of twisted pair of wires 632 which are exposed. Twisted pair of wires 632 can then be coupled with an interconnect, thereby generating a finished, functional guidewire, substantially similar in configuration to guidewire 470 (FIG. 5A) and in functionality to guidewire 100 (FIG. 1A). Additionally, an elastic polymer layer may be applied to the distal end of the guidewire. This elastic polymer layer is typically a heat shrink tube having a thickness in the order of a few microns, which provides a slick, smooth, lubricious surface.

Figure 7:
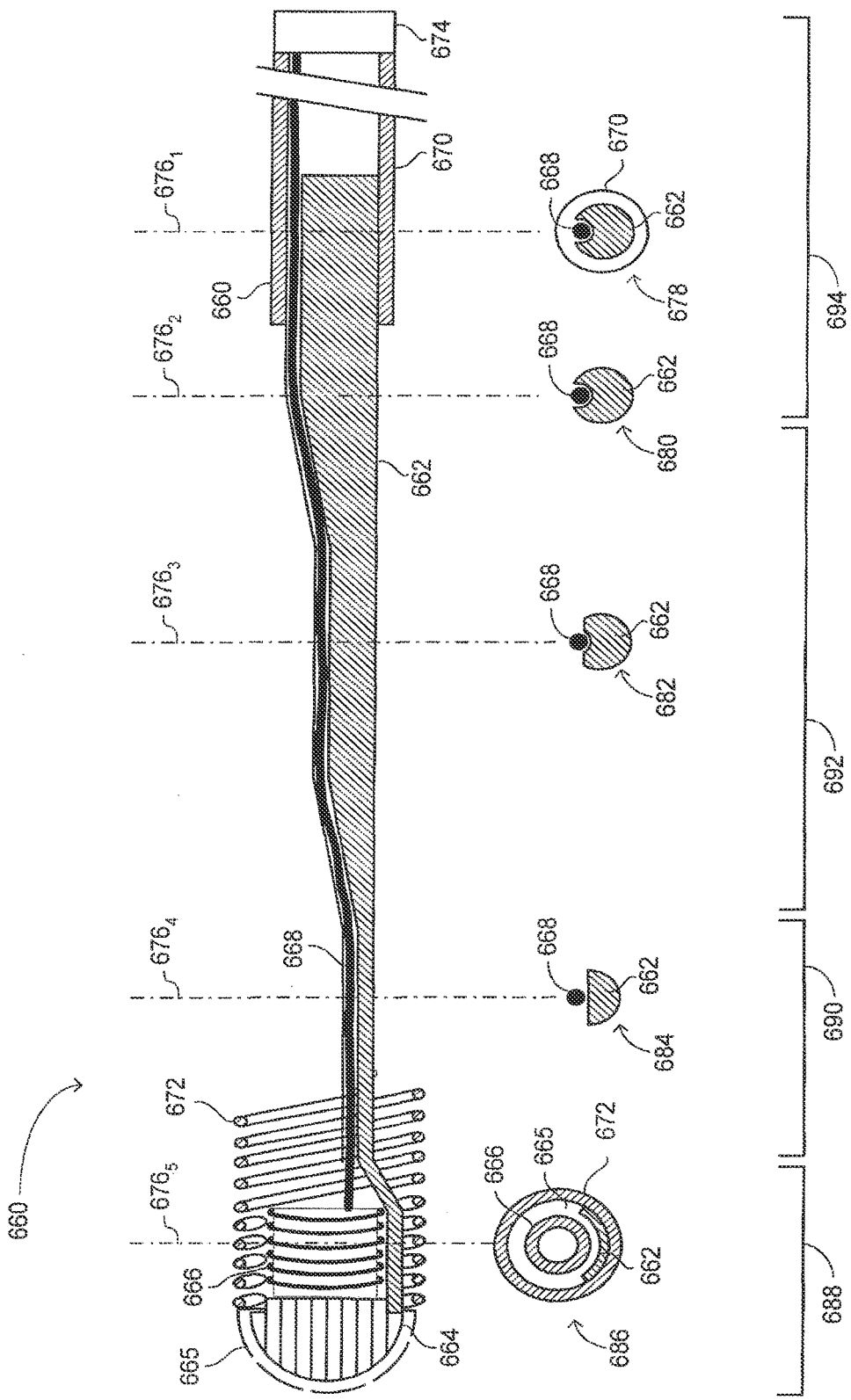
FIG. 7, is a schematic illustration of a cross sectional view of a guidewire, constructed and operative in accordance with another embodiment of the disclosed technique.

Reference is now made to FIG. 7, which is a schematic illustration of a cross sectional view of a guidewire generally referenced 660, constructed and operative in accordance with another embodiment of the disclosed technique. Guidewire 660 includes a grooved corewire 662, a plug 664, a sensor 666, a twisted pair of wires 668, referred to herein as twisted pair 668, a tubular proximal end 670 and a tubular spring 672. Grooved corewire 662 is made of metal (e.g., stainless steel, nitinol) Sensor 666 is sensor capable of measuring scalar values such as pressure and temperature as well as vector values such as position and orientation of a magnetic field. For example, sensor 66 is a coil sensor capable of measuring the strength and orientation of a magnetic field. Guidewire 660 can be coupled with an interconnect 674. Twisted pair 668 are coupled with sensor 666 and with interconnect 674. Plug 664 is coupled with the distal tip section 688 of guidewire 660. Tubular spring 670 is placed around distal sections 688 and 690 of guidewire 660. Grooved corewire 662 is coupled with tubular proximal end 670 (e.g., by bonding or welding).

In FIG. 7, dash-dot lines $676_1$, $676_2$, $676_3$, $676_4$ and $676_5$ represent lateral cross-sections of guidewire 660. Along section 694, the diameter of grooved corewire 694 remains substantially constant and is in the order of hundreds of micrometers. In first cross-section 678, the diameter of grooved corewire 662 has an initial outer diameter and is inserted into tubular proximal end 670. Twisted pair 668 are placed within a groove along grooved corewire 662. It is noted that although twisted pair 668 is an unshielded twisted pair, tubular spring 672 may provide electrical shielding for twisted pair 668. In second cross-section 680 the diameter of grooved corewire 662 has an initial outer diameter and twisted pair 668 are placed within a groove along grooved corewire 662. However, grooved corewire 662 is no longer within tubular proximal end 670.

Along section 692 of guidewire 660, the diameter of grooved corewire 662 is gradually reduced. Furthermore, the shape of the lateral cross-section of grooved corewire 662 gradually changes. In third cross-section 682 the shape of the lateral cross-section of grooved corewire 662 is that of a semi-circle. Furthermore, in third cross-section 682, the diameter of grooved corewire 662 is smaller than in first and second cross-sections 678 and 680. Along section 690, the diameter of grooved corewire 660 is substantially constant, however, this diameter is smaller than the diameter shown in cross-section 682. In forth cross-section 684 the shape of lateral cross-section of grooved corewire 662 is that of circular segment. Fifth cross-section 686 is a cross section of the distal tip of guidewire 670 (i.e. section 688). Along section 188 the residual volume between sensor 666 and tubular spring 672 is filled with a polymer bond 665, thus securing the sensor in place. In FIG. 7, the distal end of guidewire 670 is formed, according to the disclosed technique, in a manner such that it exhibits increased flexibility over the flexibility of guidewires 100 and 220. Thus the distal tip of guidewire 670 exhibits substantial maneuverability.

Reference is now made to FIGS. 8A-8E, which are schematic illustrations of a medical device, such as, for example, a guidewire 750, constructed and operative in accordance with a further embodiment of the disclosed technique. While the description below is directed to a guidewire, it will be appreciated by those having ordinary skill in the art that other medical devices may also have the same or similar construction, and be constructed in the same or similar manner. Accordingly, the present disclosure is not meant to be limited solely to guidewires, but rather a guidewire is described in detail for exemplary purposes only.

Figure 8A:
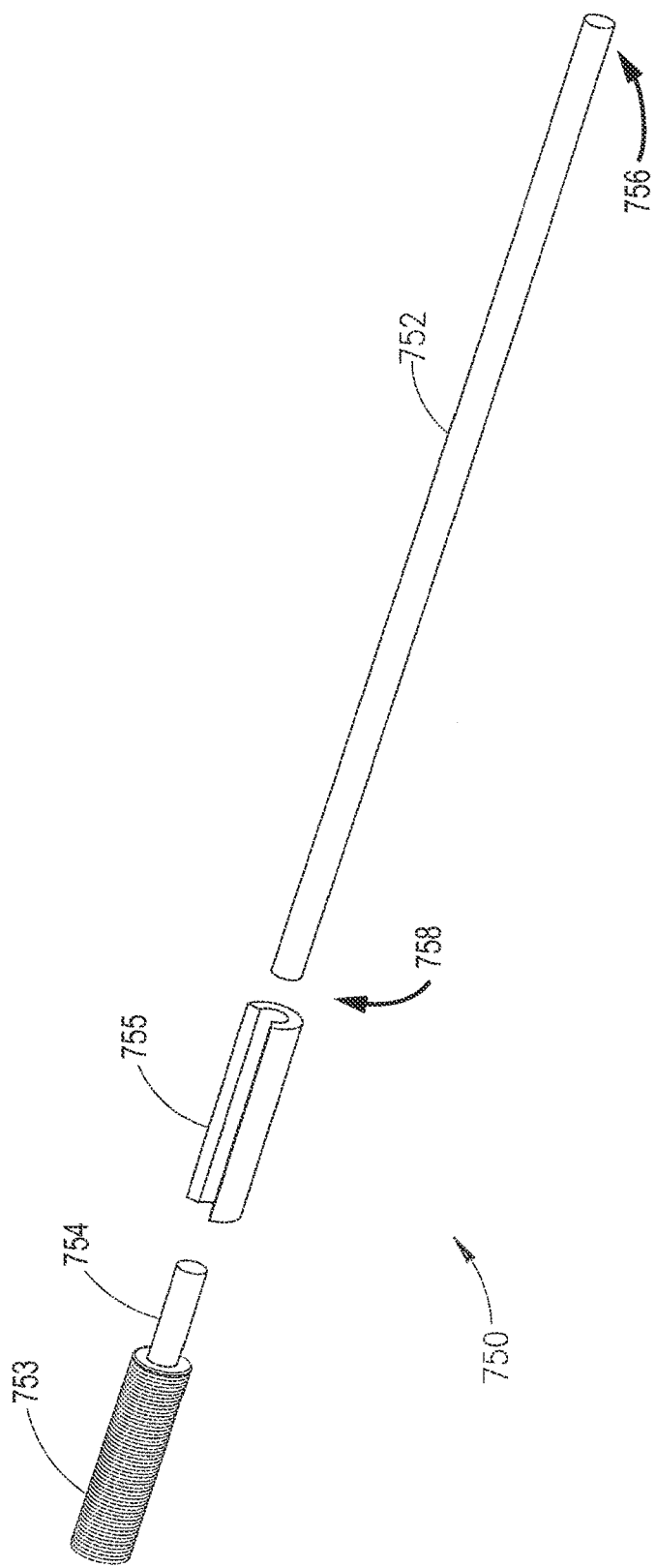
FIG. 8A is a schematic perspective exploded illustration of a guidewire, constructed and operative in accordance with a further embodiment of the disclosed technique.

FIG. 8A is a schematic perspective exploded illustration of the guidewire 750. In an exemplary embodiment, guidewire 750 includes a corewire 752, a sensor 753, a sensor core 754 and a coupler 755. Sensor 753 is coupled with a sensor core 754 (e.g., the sensor 753 may be wound onto the sensor core 754). The length of sensor core 754 is larger than the length of sensor 753. Thus, when sensor 753 is coupled with sensor core 754, sensor 753 covers only a portion of sensor core 754 such that sensor core 754 extends from one side of sensor 753. The lengths of sensor 753 and sensor core 754 are on the order of a few millimeters. For example, in one embodiment, sensor 753 has a length of 1.5 mm, and sensor core 754 has a length of 2 mm. In the illustrated embodiment, sensor 753 is a coil sensor capable of measuring the strength and orientation of a magnetic field. In general, a coil sensor can have a thickness on the order of a few hundred micrometers (e.g., 250 µm).

In an exemplary embodiment, corewire 752 is formed of stainless steel and has a proximal end 756 and a distal end 758. In an exemplary embodiment, corewire 752 has a unitary construction, however, in another exemplary embodiment, corewire 752 may be constructed of multiple segments or pieces that are bonded or otherwise coupled together. Additionally, in an exemplary embodiment, corewire 752 has a constant diameter from its proximal end 756 to its distal end 758. However, in other exemplary embodiments, the diameter of corewire 752 may vary (e.g., taper) from the proximal end to the distal end thereof. In one exemplary embodiment, the distal end 758 of corewire 752 exhibits substantially the same diameter as sensor core 754 (e.g., on the order of hundreds of micrometers).

Coupler 755 is a hollow tube with a part of the wall thereof removed along the length of coupler 755. The inner diameter of coupler 755 is substantially similar to the diameters of sensor core 754 and the distal end 758 of corewire 752. In an exemplary embodiment, coupler 755 is formed of stainless steel. In other exemplary embodiments, coupler 755 may have a construction other than that described above. For example, in another exemplary embodiment, coupler 755 may have a whole tube construction, and/or may be formed of material(s) other than stainless steel. Accordingly, those having ordinary skill in the art will appreciate that guidewires comprising a coupler having a construction other than a hollow tube with a part of the wall thereof removed and being formed of materials other than stainless steel remain within the spirit and scope of the present disclosure.

Figure 8B:
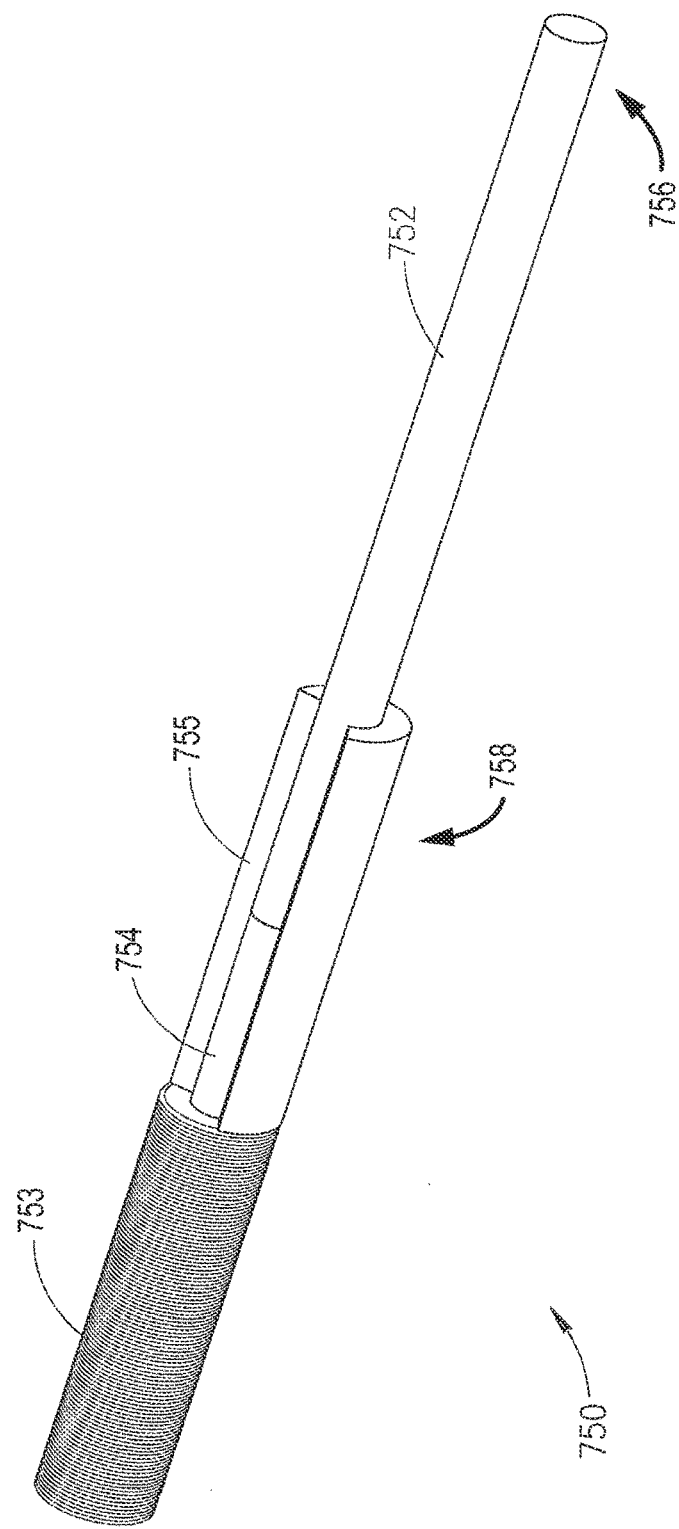
FIG. 8B is a schematic perspective illustration of the guidewire illustrated in FIG. 8A at an intermediate stage of assembly.
Figure 8C:
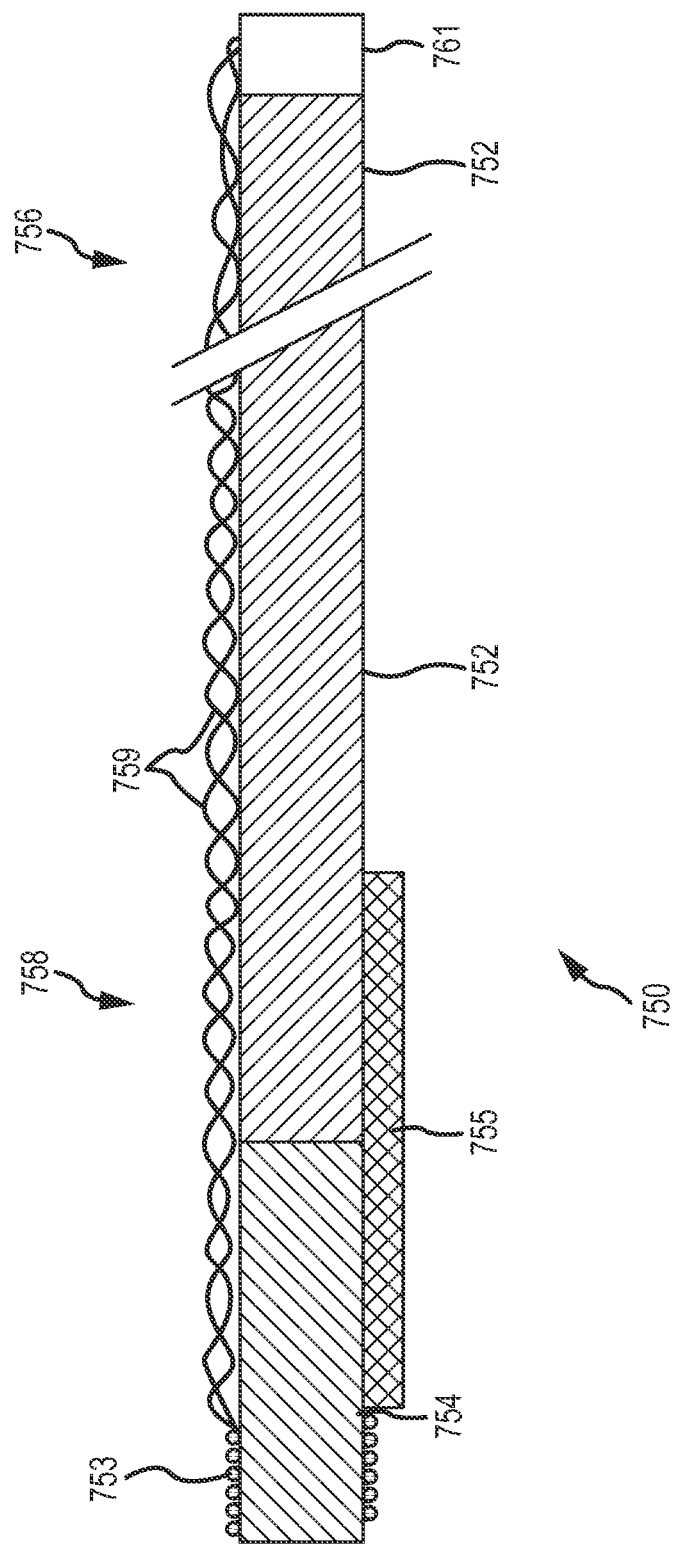
FIG. 8C is a schematic illustration of a cross-sectional view of the guidewire illustrated in FIGS. 8A and 8B at an intermediate stage of assembly.
Figure 8D:
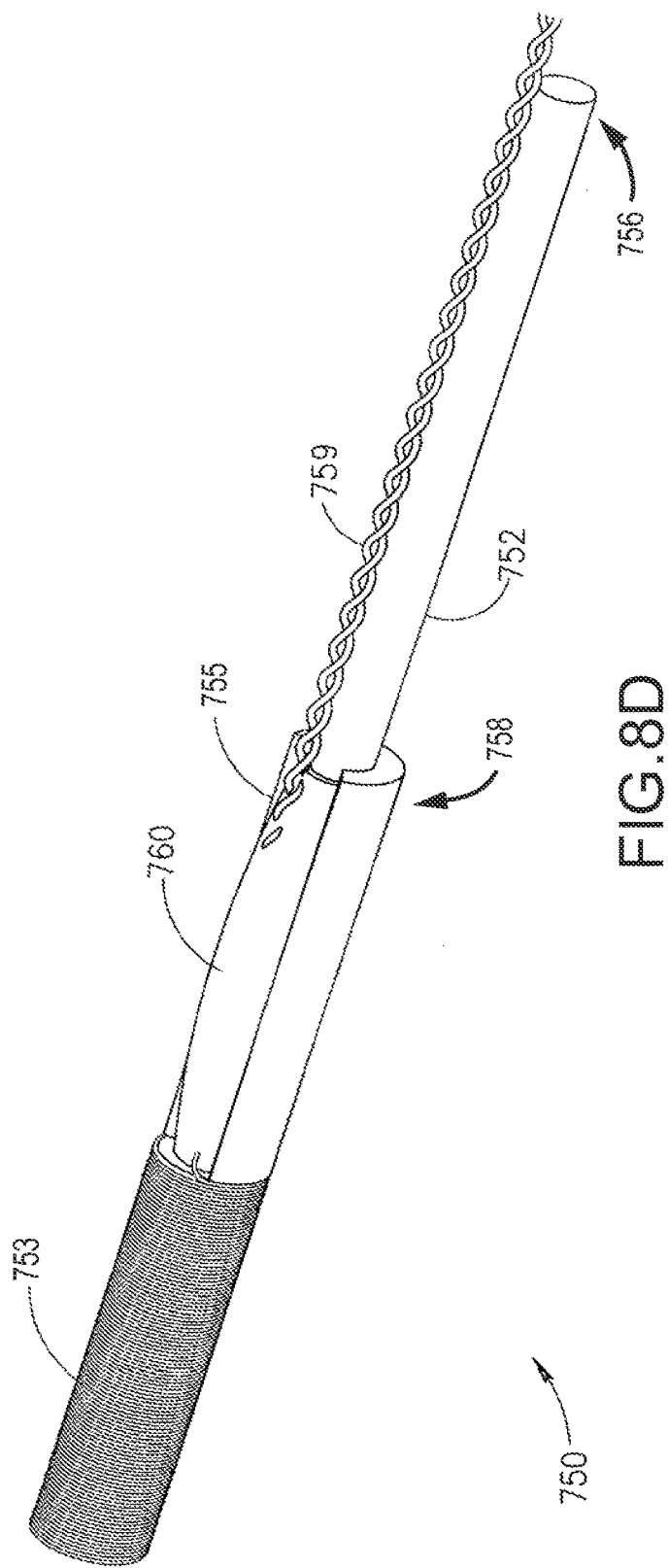
FIG. 8D is a schematic perspective illustration of the guidewire illustrated in FIGS. 8A-8C at an intermediate stage of assembly.

FIG. 8B is a schematic perspective illustration, and FIG. 8C is a schematic illustration of a cross-sectional view, of guidewire 750 at an intermediate stage of assembly. In FIGS. 8B and 8C, the distal end 758 of corewire 752 is inserted into one side of coupler 755. The portion of sensor core 754 that is not covered by sensor 753 is inserted into the other side of coupler 755. FIG. 8D is a schematic perspective illustration of guidewire 750 at a further intermediate stage of assembly. In FIG. 8D, a twisted pair of wires 759 are electrically connected to sensor 753 (e.g., soldered), and mechanically coupled to sensor 753 by a coupling material 760. Twisted pair 759 may be coupled at the proximal end 756 of corewire 752 with an interconnect 761 (best shown in FIG. 8C) which enables twisted pair 759, and thus sensor 753, to be coupled with other devices, such as a computer, a power source, a device measuring magnetic field strength and orientation, a visualization, navigation, and/or mapping system, and the like. In addition to mechanically coupling the twisted pair 759 to sensor 753, coupling material 760 is also operative to couple sensor core 754 and corewire 752 with coupler 755. In an exemplary embodiment, coupling material 760 comprises an adhesive, such as, for example and without limitation, epoxy or cyanoacrylate adhesives. It will be appreciated, however, that in other exemplary embodiments, adhesives other than those specifically identified above may be used, and therefore, guidewires having coupling materials other than epoxy or cyanoacrylate adhesives remain within the spirit and scope of the present disclosure.

Figure 8E:
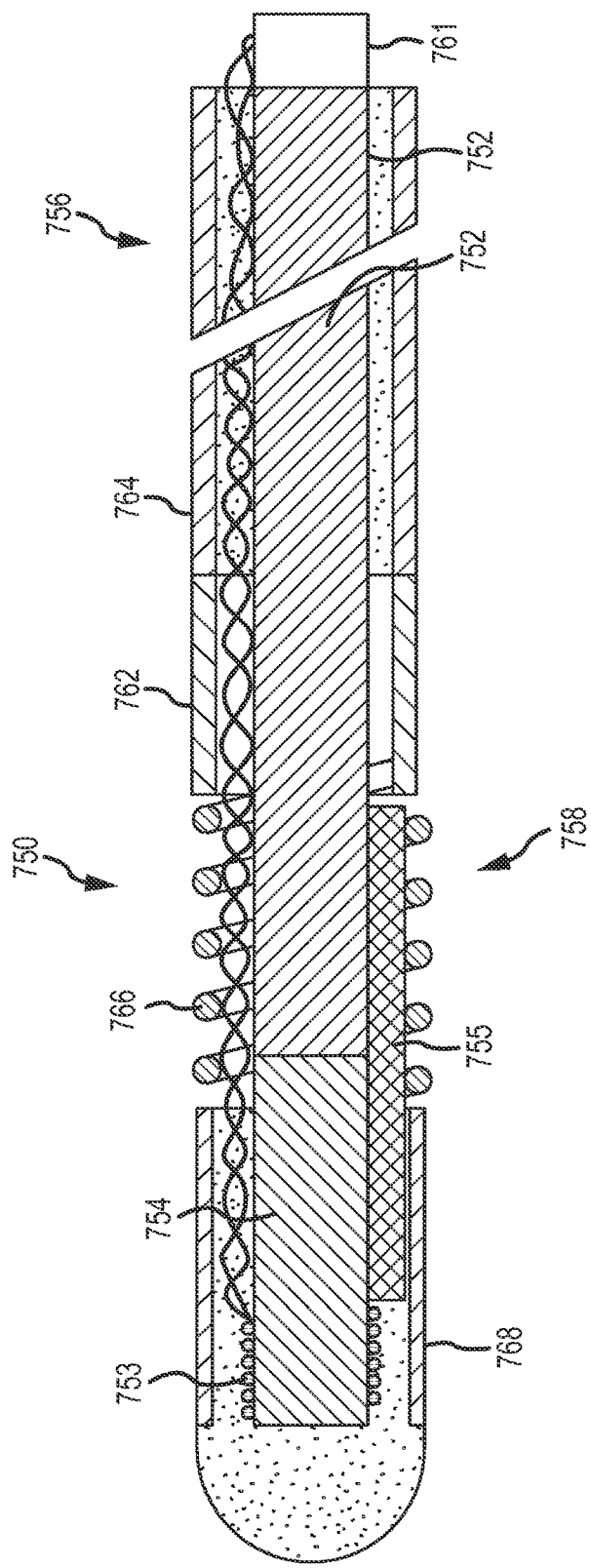
FIG. 8E is a schematic illustration of a cross-sectional view of the guidewire illustrated in FIGS. 8A-8D at a near final stage of assembly.

With reference to FIG. 8E, which is a schematic illustration of a cross-sectional view of guidewire 750 near a final stage of assembly, in an exemplary embodiment, guidewire 750 may further include one or more thin elastic polymer layers 762 disposed over one or more portions of corewire 752, sensor 753, sensor core 754, and/or coupler 754. In the exemplary embodiment illustrated in FIG. 8E, polymer layer 762 is disposed over a portion of corewire 752 near the distal end 758 thereof, and therefore, twisted pair 759. Polymer layer 762 may comprise a heat shrink tube (such as, for example, a hydrophilic tube) of a few microns thickness, which provides a slick, smooth and lubricious surface. In an embodiment, wherein polymer layer 762 comprises a heat shrink tube, the tube is configured to shrink when exposed to a sufficient amount of heat during a heating process performed during the assembly of guidewire 750. In an exemplary embodiment, polymer layer 762 may comprise an epoxy, cyanoacrylate, or a ultra-violet (UV) curing adhesive. The present disclosure is not meant to be limited to such materials, however, and guidewires having a polymer layer comprising materials other than those specifically identified above remain within the spirit and scope of the present disclosure.

In an exemplary embodiment, and with continued reference to FIG. 8E, guidewire 750 may further include one or more layers of metallic material 764 disposed over one or more portions of corewire 752, sensor 753, sensor core 754, and/or coupler 755. In the exemplary embodiment illustrated in FIG. 8E, guidewire 750 includes one metallic layer 764 disposed over a portion of corewire 752 near the distal end 758 thereof, and therefore, twisted pair 759. In an exemplary embodiment, the metallic layer 764 comprises a hypotube formed of, for example, stainless steel, and is coupled to corewire 752. In one embodiment provided for exemplary purposes only, metallic layer 764 is coupled to corewire 752 using, for example, an adhesive such as those described above. In an exemplary embodiment, metallic layer 764 extends from the proximal end of guidewire 750 to a point at or near the distal end thereof. For example, in the embodiment illustrated in FIG. 8E wherein guidewire 750 includes both polymer layer 762 and metallic layer 764, metallic layer 764 extends from the proximal end of guidewire 750 to polymer layer 762 disposed at or near the distal end of guidewire 750. Accordingly, in such an embodiment, metallic layer 764 is disposed proximate and adjacent to polymer layer 762, and the respective layers may be bonded or otherwise coupled together using, for example, an adhesive such as those described above.

With continued reference to FIG. 8E, in an exemplary embodiment, guidewire 750 may still further include one or more tubular springs 766 covering or circumscribing one or more portions of corewire 752, sensor 753, sensor core 754, and/or coupler 755. Tubular spring 766 is a tube exhibiting lateral flexibility (i.e., perpendicular to the central axis of the tube) made of a metal (e.g., stainless steel, platinum, iridium, nitinol), a flexible polymer tube, or a braided or coiled plastic tube. In an exemplary embodiment, spring 766 comprises a radiopaque material so as to allow for the visualization of the spring, and therefore, the guidewire 750, when used with an x-ray-based visualization system, such as, for example, fluoroscopy. Tubular spring 766, which has a length on the order of centimeters, maintains the outer diameter of guidewire 750 over the length thereof, supports compressive loads, and resists buckling of the guidewire 750 without substantially increasing torsional and bending stiffness.

In an exemplary embodiment, spring 766 is rigidly coupled with sensor 753. More particularly, one end of spring 766 is bonded to sensor 753. As with the coupling of sensor core 754 and corewire 752 with coupler 755, spring 766 may be coupled with sensor 753 with an adhesive, such as, for example and without limitation, those described above (e.g., epoxy or cyanoacrylate adhesives). In another exemplary embodiment, and as illustrated in FIG. 8E, rather than coupling one end of spring 766 directly to sensor 753, a cylindrical metal shroud 768 covers sensor 753 and spring 766 is bonded to shroud 768 using, for example, an adhesive such as those described above. In an exemplary embodiment, the end of spring 766 opposite the end bonded to sensor 753 or shroud 768 is coupled with polymer layer 762 or metallic layer 763 described above using, for example, an adhesive such as those described above. In an exemplary embodiment, and as illustrated in FIG. 8E, the same type of adhesive used to bond spring 766 to sensor 753 and/or shroud 766, for example, may also be used to form a rounded, ball point-type tip at the extreme distal end of the guidewire 750.

In an exemplary embodiment, guidewire 750 may further comprise an outer polymer layer (not shown) extending from the extreme proximal end to the extreme distal end of guidewire such that substantially the entire assembly is covered with the outer polymer layer. The outer polymer layer provides added lubricity and hydrophilic properties, and/or forms a substantially smooth external surface of guidewire 750.

Figure 9B:
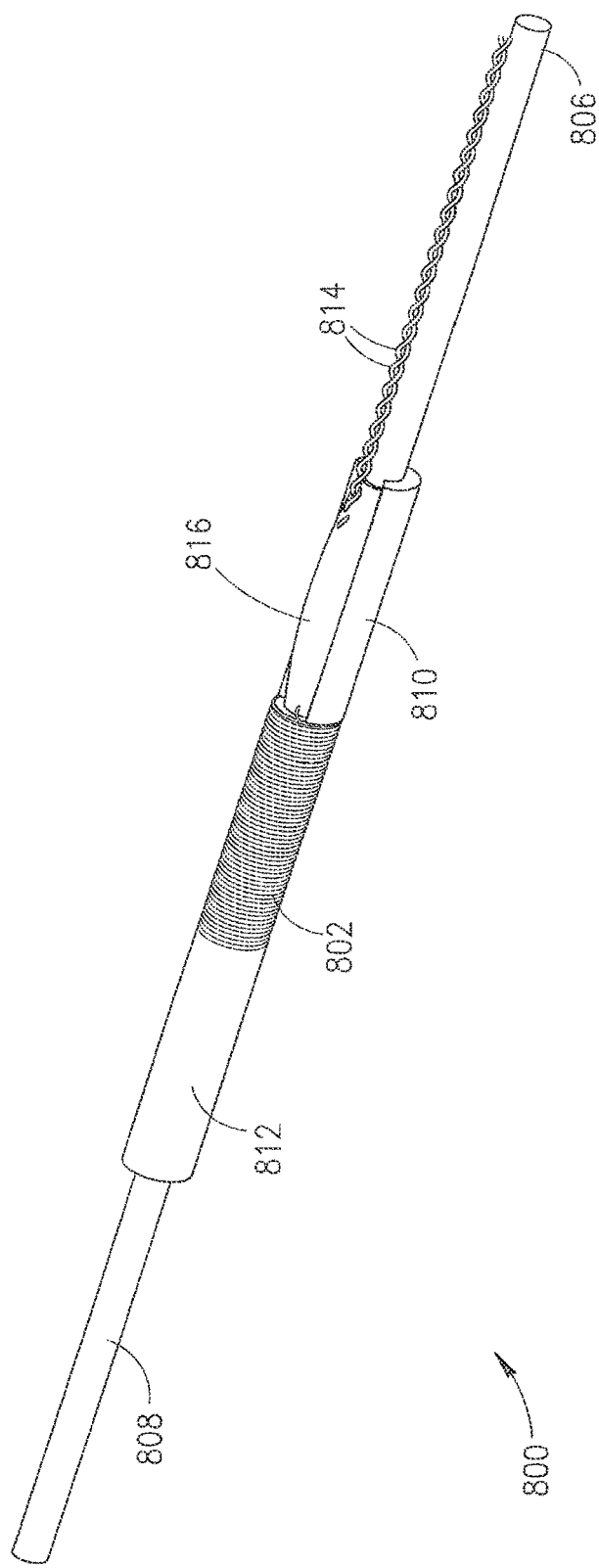
FIG. 9B is a schematic perspective illustration of the guidewire illustrated in FIG. 9A at an intermediate stage of assembly.

Reference is now made to FIGS. 9A and 9B, which are schematic perspective illustrations of a guidewire, generally reference 800, constructed and operative in accordance with a further embodiment of the disclosed technique. FIG. 9A is a schematic perspective exploded illustration of the guidewire 800. Guidewire 800 includes a first corewire 806, a second corewire 808, a sensor 802, a sensor core 804, a first coupler 810, and a second coupler 812. With respect to at least first corewire 806, sensor 802, sensor core 804, and first coupler 810, the description above relating to the embodiment illustrated in FIGS. 8A-8E applies here with equal force, and therefore, will not be repeated in its entirety.

As illustrated in FIGS. 9A and 9B, sensor 802 is coupled with sensor core 804 (e.g., the sensor 802 is wound onto the sensor core 804). The length of sensor core 804 is larger than the length of sensor 802. Thus, when sensor 802 is coupled with sensor core 804, sensor 802 covers only a portion of sensor core 804 such that sensor core 804 extends from both sides of sensor 802. As with the sensor 753 and sensor core 754 described above, the lengths of sensor 802 and sensor core 804 are on the order of a few millimeters. In FIGS. 9A and 9B, sensor 802 is a coil sensor. However, sensor 802 may be any other type of sensor capable of measuring scalar or vector values.

As illustrated in FIG. 9A, at least portions of first and second corewires 806 and 808 and sensor core 804 exhibit substantially the same diameter (e.g., on the order of hundreds of micrometers). As with coupler 755 described above, in an exemplary embodiment, first coupler 810 is a hollow tube with a part of the wall thereof removed along the length of first coupler 810. In an exemplary embodiment, second coupler 812 is a whole hollow tube. The inner diameters of first coupler 810 and second coupler 812 are substantially similar to the diameters of at least portions of first and second corewires 806 and 808 and the diameter of sensor core 804. It will be appreciated by those having ordinary skill in the art that in other exemplary embodiments, the construction of first and second couplers 810, 812 may be reversed, or both of couplers 810, 812 may share a common construction (e.g., both may be whole tubes, or both may be hollow tubes with parts of the walls thereof removed along the lengths of the respective couplers). Additionally, in an exemplary embodiment, couplers 810, 812 are formed of stainless steel. However, in other exemplary embodiments, one or both of couplers 810, 812 may be formed of a material other than stainless steel. Accordingly, embodiments of guidewire 800 wherein the first and second couplers 810, 812 have a construction other than those illustrated in FIGS. 9A and 9B and specifically described above, remain within the spirit and scope of the present disclosure.

FIG. 9B is a schematic perspective illustration of guidewire 800 at an intermediate stage of assembly. In FIG. 9B, and as was described above with respect to the embodiment illustrated in FIGS. 8A-8E, a twisted pair of wires 814 are electrically connected to sensor 802 (e.g., soldered) and mechanically coupled to sensor 802 by a coupling material 816, such as, for example and without limitation, epoxy or cyanoacrylate adhesives. First corewire 806 is inserted into one side of first coupler 810. One side of sensor core 804 is inserted into the other side of first coupler 810. As was also described above, corewire 806, first coupler 810, and sensor core 804 are bonded together by coupling material 816 such as, for example, an epoxy or cyanoacrylate adhesive. The other side of sensor core 804 is inserted into one side of second coupler 812. Second corewire 808 is inserted into the other side of second coupler 812. An adhesive, such as, for example and without limitation, an epoxy or cyanoacrylate adhesive, is used to couple the sensor core 804 and the second corewire 808 with the second coupler 812. Thus, rather than the sensor of the guidewire being disposed at the distal end thereof, in this embodiment, sensor 802 is positioned anywhere along the length of guidewire 800.

As with the embodiment described above with respect to FIGS. 8A-8E, twisted pair 814 may be coupled at the proximal end of guidewire 800 with an interconnect (not shown) which enables twisted pair 814, and thus sensor 802, to be coupled with other devices. Additionally, similar to the description above relating to the embodiment illustrated in FIGS. 8A-8E, guidewire 800 may include one or more elastic polymer layers, metallic layers, tubular springs, and/ or shrouds (not shown) disposed over one or more portions of corewires 806, 808, sensor 802, sensor core 804, and or couplers 810, 812. The respective descriptions above relating to the composition and arrangement of polymer layer 762, metallic layer 763, tubular spring 766, and shroud 768 apply here with equal force, and therefore, will not be repeated.

Further, in an exemplary embodiment, guidewire 800 may comprise an outer polymer layer (not shown) extending from the extreme proximal end to the extreme distal end of guidewire such that substantially the entire assembly is covered with the outer polymer layer. The outer polymer layer provides added lubricity, hydrophilic properties, and/ or forms a substantially smooth external surface of guidewire 800.

Figure 10:
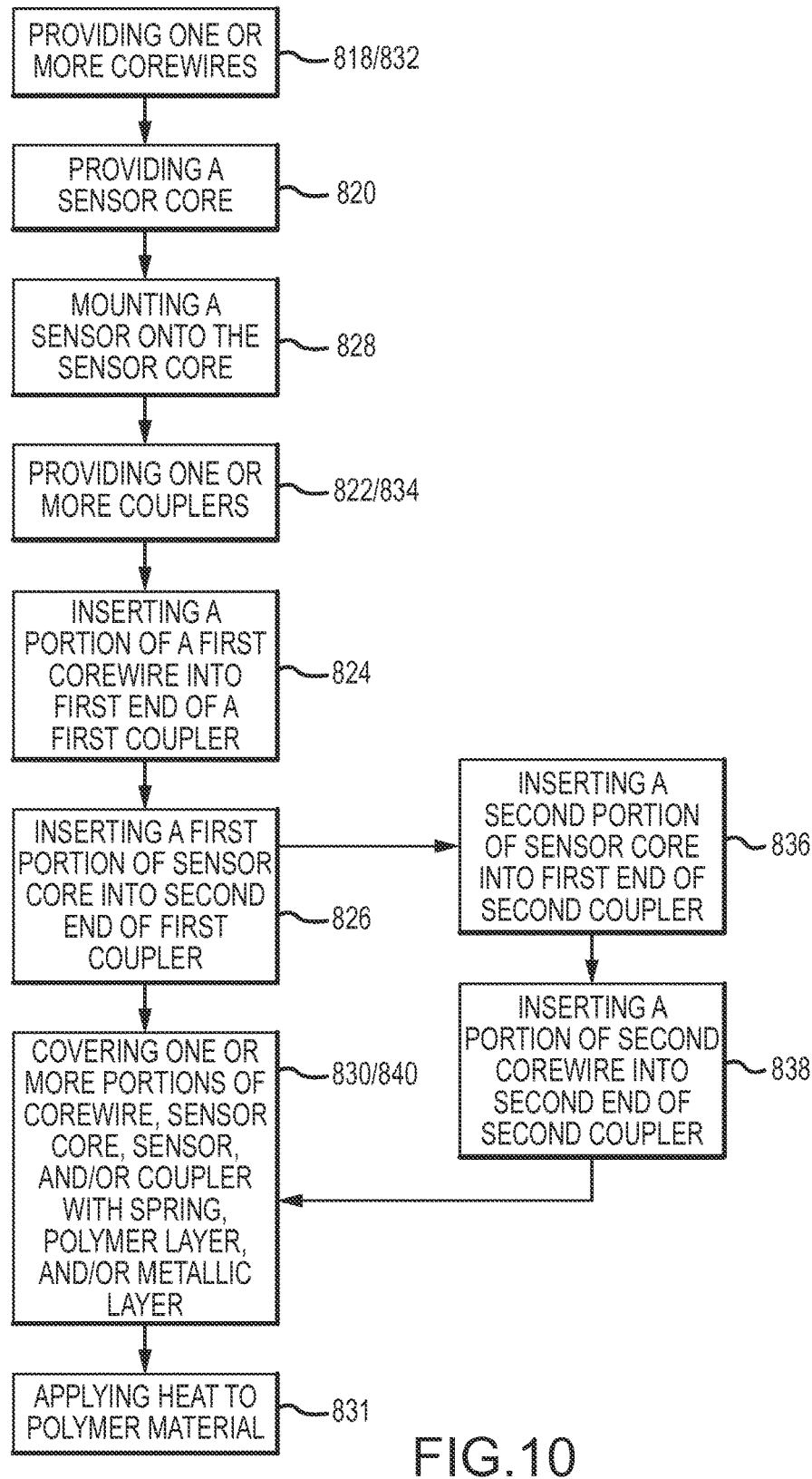
FIG. 10 is a flow chart diagram illustrating an exemplary embodiment of a method of manufacturing the guidewires illustrated in FIGS. 8A-9B in accordance with the present teachings.

With reference to FIG. 10, in addition to the structure of guidewires 750, 800, it will be appreciated that another aspect of the present disclosure is a method of manufacturing a medical device, such as, for example, guidewires 750, 800 described above. In an exemplary embodiment, the method comprises a step 818 of providing a corewire, such as, for example, corewires 752, 806 described above. A step 820 comprises providing a sensor core, such as, for example, sensor cores 754, 804 described above, configured to have a sensor mounted thereon. The method further comprises a step 822 of providing a coupler, such as, for example, couplers 755, 810 described above, configured to couple the corewire with the sensor core. In an exemplary embodiment, the method still further comprises a step 824 of inserting a portion of the sensor core into a first end of the sensor core, and a step 826 of inserting a portion of the sensor core into a second end of the coupler. The method may further comprise bonding each of the sensor core and the corewire to the coupler using, for example, adhesives such as those described above.

With continued reference to FIG. 10, in an exemplary embodiment, the method further comprises a step 828 of mounting a sensor, such as, for example, sensors 753, 802 described above, onto the sensor core. The method may further comprise a step of connecting the sensor to a sensor wire, such as, for example, a twisted pair of wires. In an exemplary embodiment, the method further comprises a step 830 of covering a portion of at least one of the corewire, coupler, and sensor core with an elastic polymer material, a metallic material, and/or a tubular spring, as described in greater detail above.

In an exemplary embodiment wherein the guidewire comprises a layer of elastic polymer material, and the polymer material, in turn, comprises a heat shrink material, the method further comprises a step 831 of applying heat to the guidewire to cause the polymer material to shrink.

In an exemplary embodiment, the method further comprises steps 832, 834 of providing a second corewire, such as, for example, corewire 808 described above, and a second coupler, such as, for example, coupler 812 described above. In such an embodiment, the method still further comprises a step 836 of inserting a second portion of the sensor core into a first end of the second coupler, and a step 838 of inserting a portion of the second corewire into a second end of the second coupler. In an exemplary embodiment, the method further comprises bonding the second corewire and the sensor core to the second coupler using, for example, an adhesive such as those described above. In an exemplary embodiment, the method may still further comprise a step 840 of covering a least a portion of the second coupler, the sensor core, and the second corewire with a polymer material, a metallic material, and/or a tubular spring, such as, for example, the polymer layer, metallic layer, and springs described above.

In an exemplary embodiment, and whether the guidewire comprises one or two corewires or couplers, the method further comprises covering substantially the entire guidewire assembly with a polymer material to form an outer polymer layer.

It will be appreciated that in other exemplary embodiments, the methodology described above may further include steps not specifically described with respect to FIG. 10, but described elsewhere with respect to FIGS. 8A-9B. Accordingly, embodiments of the method comprising such steps remain within the spirit and scope of the present disclosure.

Figure 11A:
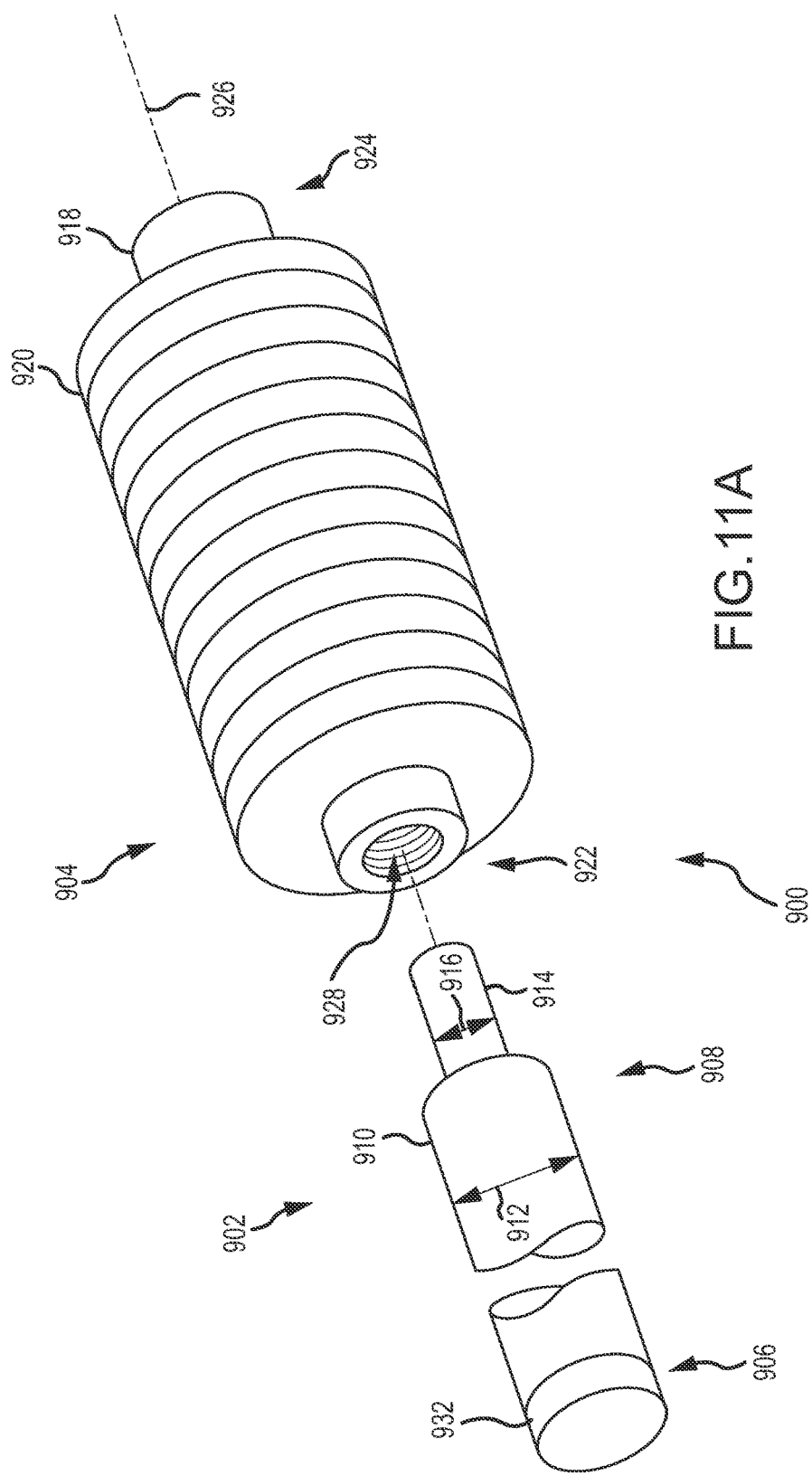
FIG. 11A is schematic perspective exploded illustration of a portion of a guidewire constructed and operative in accordance with yet a further embodiment of the disclosed technique.
Figure 11B:
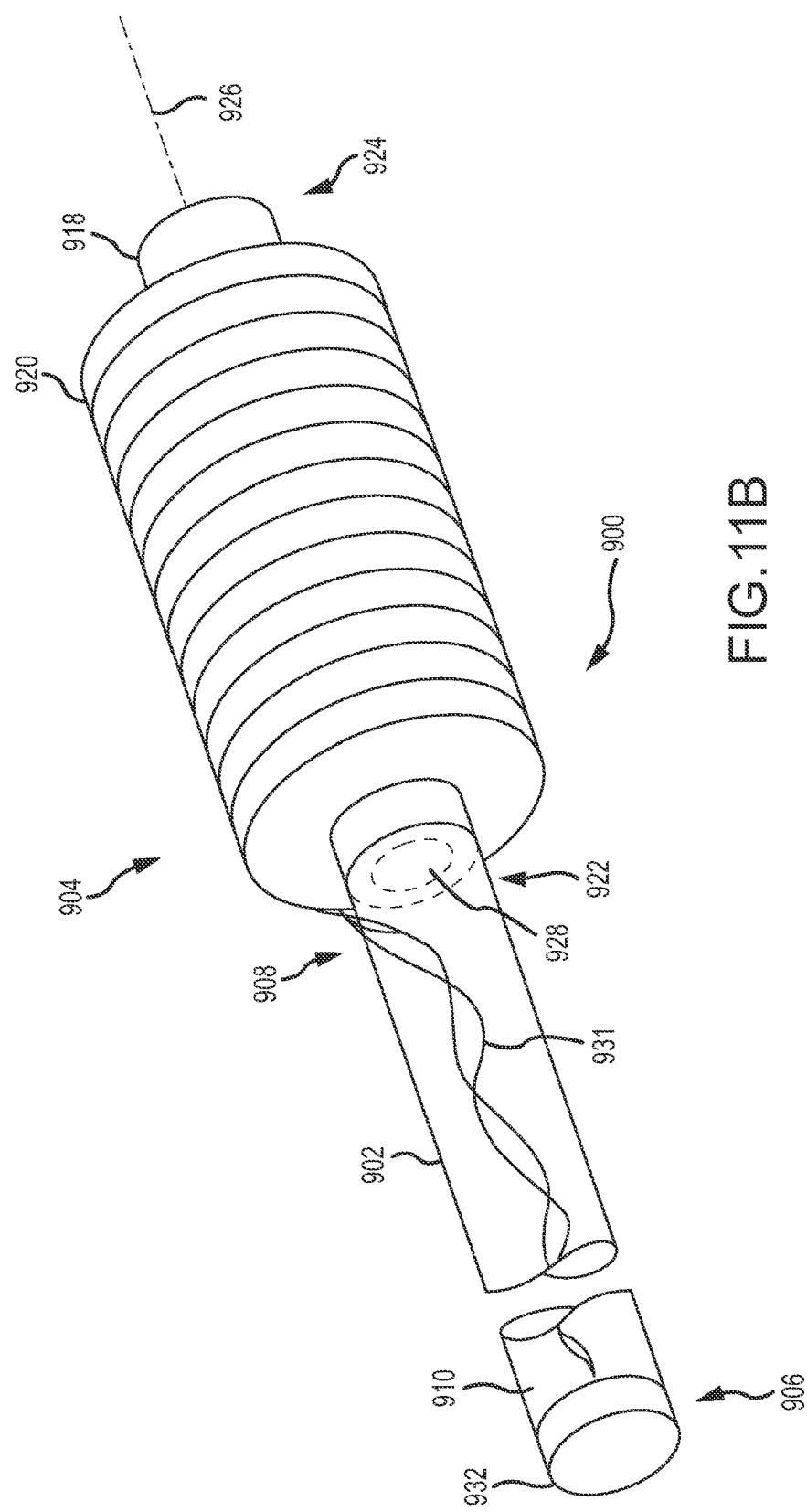
FIG. 11B is a schematic perspective illustration of the guidewire illustrated in FIG. 11A at an intermediate stage of assembly.

Reference is now made to FIGS. 11A and 11B, which are schematic perspective illustrations of a guidewire 900 constructed and operative in accordance with yet another embodiment of the present disclosure. While the description below is directed to a guidewire, it will be appreciated by those having ordinary skill in the art that other medical devices may also have the same or similar construction, and be constructed in the same or similar manner. Accordingly, the present disclosure is not meant to be limited solely to guidewires, but rather a guidewire is described for exemplary purposes only.

FIG. 11A is a schematic perspective exploded illustration of the guidewire 900. The guidewire 900 comprises a corewire 902 and a sensor assembly 904. Corewire 902, which may be constructed of, for example and without limitation, stainless steel, has a proximal end 906 and a distal end 908. In an exemplary embodiment, corewire 902 has a unitary construction, however, in another exemplary embodiment, corewire 902 may be constructed of multiple segments or pieces that are bonded or otherwise coupled together. Whether formed of one or multiple segments or pieces, in an exemplary embodiment corewire 902 comprises two portions. A first portion 910 extends from proximal end 906 to a point near distal end 908. In an exemplary embodiment, first portion 910 of corewire 902 tapers from proximal end 906 thereof to a point near distal end 908. In an exemplary embodiment, the diameter (i.e., diameter 912) near the end of first portion 910 is on the order of 0.1-0.2 mm. A second portion 914 of corewire 902 extends from the distal end point of first portion 910 to the most distal point of corewire 902 at distal end 908. Second portion 914 has a diameter 916 that is less than diameter 912 of first portion 910. In one embodiment provided for exemplary purposes only, diameter 912 is on the order of 0.05-0.08 mm. As will be described in greater detail below, second portion 914 of corewire 902 is configured to be coupled with sensor assembly 904.

With continued reference to FIG. 11A, in an exemplary embodiment, sensor assembly 904 comprises a sensor core 918 and a sensor 920 mounted on sensor core 918. Sensor core 918 has a first end 922 and a second end 924, and defines a longitudinal axis 926 extending through both first and second ends 922, 924. In an exemplary embodiment, sensor core 918 is constructed of a metallic material that displays high ferromagnetic properties (e.g., iron, nickel, alloys, and the like). Additionally, in an exemplary embodiment, sensor core 918 has an outer diameter that is substantially equal to diameter 912 of first portion 910 of corewire 902 (e.g., on the order of 0.1-0.2 mm). As illustrated in FIG. 11A, the length of sensor core 918 is larger than that of sensor 920. Thus, when sensor 920 is coupled with sensor core 918, sensor 920 covers only a portion of sensor core 918 such that sensor core 918 extends from one or both sides of sensor 920 at first and/or second ends 922, 924 of sensor core 918.

Sensor core 918 includes a bore 928 disposed within first end 922 thereof along longitudinal axis 926. In an exemplary embodiment, bore 928 is a closed bore (i.e., bore 928 does not extend from first end 922 of sensor core 918 through second end 924 thereof). In such an embodiment, bore 928 may have a depth on the order of, for example and without limitation, 0.1-0.3 mm. In another exemplary embodiment, however, bore 928 is a through bore extending from first end 922 of sensor core 918 through second end 924. Bore 928 may be formed by performing a drilling operation on first end 922 of sensor core 918, or it may be formed during the construction of sensor core 918. In any event, bore 928 is sized and configured to receive second portion 914 of corewire 902. Therefore, bore 928 has a diameter that is substantially similar to diameter 916 of the second portion 914 of the corewire 902 (e.g., on the order of 0.05-0.08 mm). Accordingly, when assembled, and as illustrated in FIG. 11B, second portion 914 of corewire 902 is disposed within bore 928 of sensor core 918. In an exemplary embodiment, second portion 914 of corewire 902 is bonded to sensor core 918 by an adhesive such as, for example, epoxy or cyanoacrylate adhesives described above.

It will be appreciated that while in the illustrated embodiment a reduced diameter portion of corewire 902 is configured to be inserted into and disposed within bore 928 of sensor core 918, in another exemplary embodiment, corewire 902 does not have a defined reduced diameter portion at distal end 908 thereof, but rather corewire 902 has a uniform diameter throughout, or tapers from proximal end 906 to distal end 908. In such an embodiment, bore 928 in sensor core 918 would be sized so as to receive distal end 908 of corewire 902. Accordingly, in any embodiment, bore 928 is sized so as to receive the extreme distal end 908 of corewire 902, regardless of whether it has the same or different diameter as the rest of corewire 902.

Figure 11C:
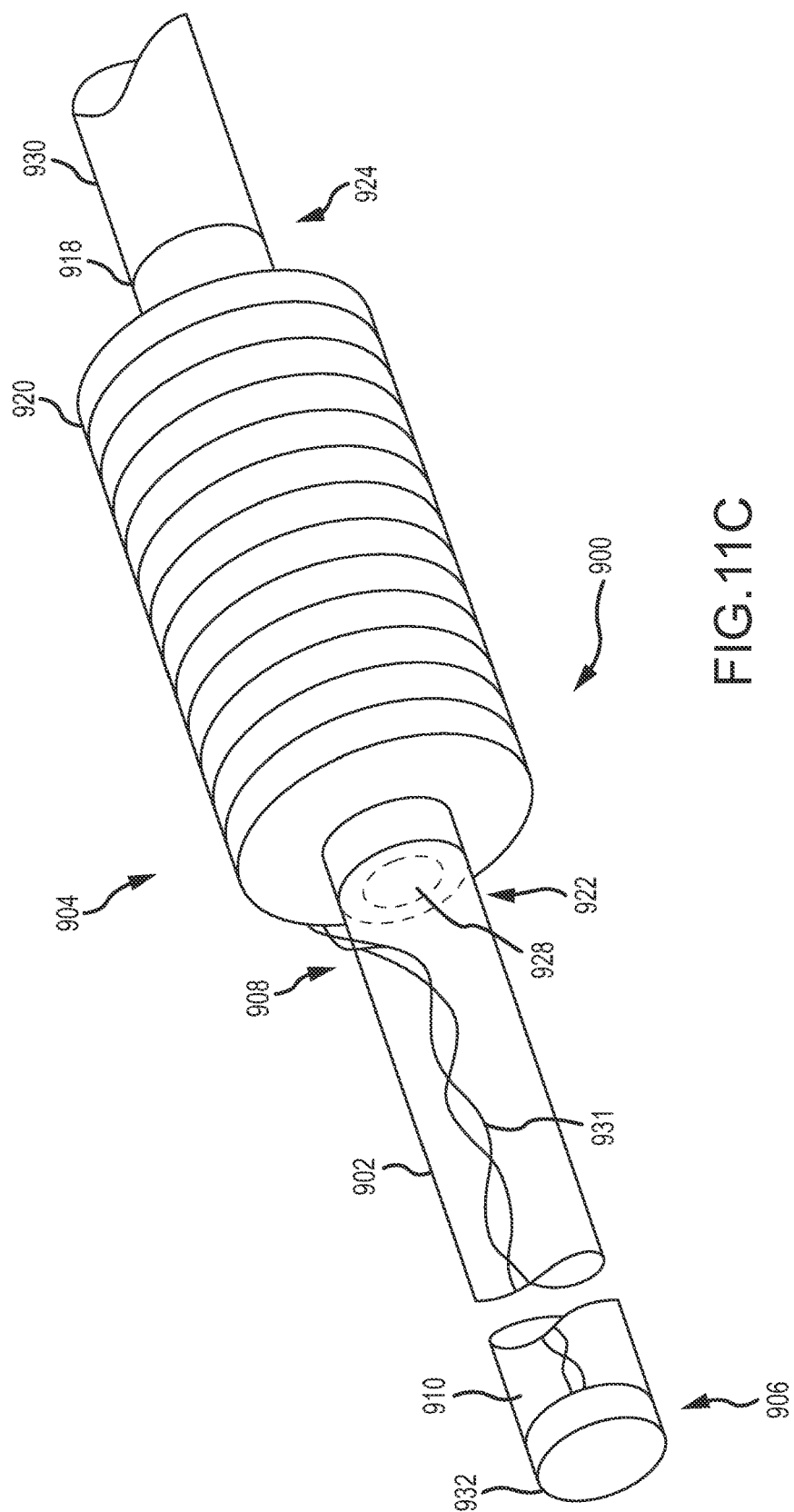
FIG. 11C is a schematic illustration of another exemplary embodiment of the guidewire illustrated in FIGS. 11A and 11B at an intermediate stage of assembly.

With reference to FIG. 11C, and as with the embodiment described above with respect to FIGS. 9A and 9B, in an exemplary embodiment, guidewire 900 may include a second corewire 930 coupled with sensor core 918. In such an embodiment, bore 928 would extend through core 918 from first end 922 to second end 924, or sensor core 918 would include a second bore in second end 922 of the sensor core 918. In either embodiment, one end of second corewire 930 would have a diameter that is substantially similar to that of the bore in second end 922 of sensor core 918 such that a portion of corewire 930 could be inserted into the bore. Accordingly, the second corewire 930 may have a reduced diameter portion (similar to that of corewire 908), or may simply have a diameter sized so as to allow for corewire 930 to be inserted into the bore. As was described in great detail above with respect to corewire 902, in an exemplary embodiment, corewire 930 is bonded to sensor core 918 by an adhesive, such as, for example, epoxy or cyanoacrylate adhesives.

Whether guidewire 900 has one or two corewires, it may have an additional sensor and sensor core attached thereto in the manner described herein. For example, a first sensor core 918 may have a through bore 928 therein that corewire 902 passes through, to where second portion 916 of corewire 902 then is inserted into bore 928' (not shown) of a second sensor core 918' (not shown). Both sensor cores 918, 918' would then have sensors 920, 920', respectively, affixed thereto. Likewise, corewire 902 may be joined to a first sensor core 918 as shown in FIG. 11A at bore 928, with a second corewire 930 joined at its proximal end to the distal end of sensor core 918. The second corewire 930 is then joined at its distal end to a bore 928' (not shown) of a second sensor core 918' (not shown).

With reference to FIGS. 11B and 11C, whether the guidewire 900 has one or two corewires, sensor assembly 904 includes a sensor 920 mounted on sensor core 918. In one embodiment provided for exemplary purposes only, sensor 920 comprises an electromagnetic field detector. In such an embodiment, sensor 920 comprises an electromagnetic coil wound around sensor core 918. In one embodiment provided for exemplary purposes only, sensor 920 has a length on the order of 1-2 mm, and an outer diameter on the order of 0.25 mm. While sensor 920 has been described above as comprising an electromagnetic field detector, it will be appreciated by those having ordinary skill in the art that in other exemplary embodiments, sensors other than electromagnetic field detectors may be mounted on sensor core 918. Therefore, a sensor comprising an electromagnetic field detector is described for exemplary purposes only and is not meant to be limiting in nature.

Whether sensor 920 comprises an electromagnetic field detector or otherwise, sensor 920 may be electrically connected (e.g., soldered) to a twisted pair of wires 931. Twisted pair 931 may extend the length of corewire 902 from sensor 920 at distal end 908 thereof, to proximal end 906. In such an embodiment, twisted pair 931 may be electrically connected to an interconnect 932, thereby enabling twisted pair 931, and thus sensor 920, to be coupled with other devices, such as, for example and without limitation, a computer, a power source, a device measuring magnetic field strength and orientation, a visualization, navigation, and/or mapping system, and the like.

Figure 11D:
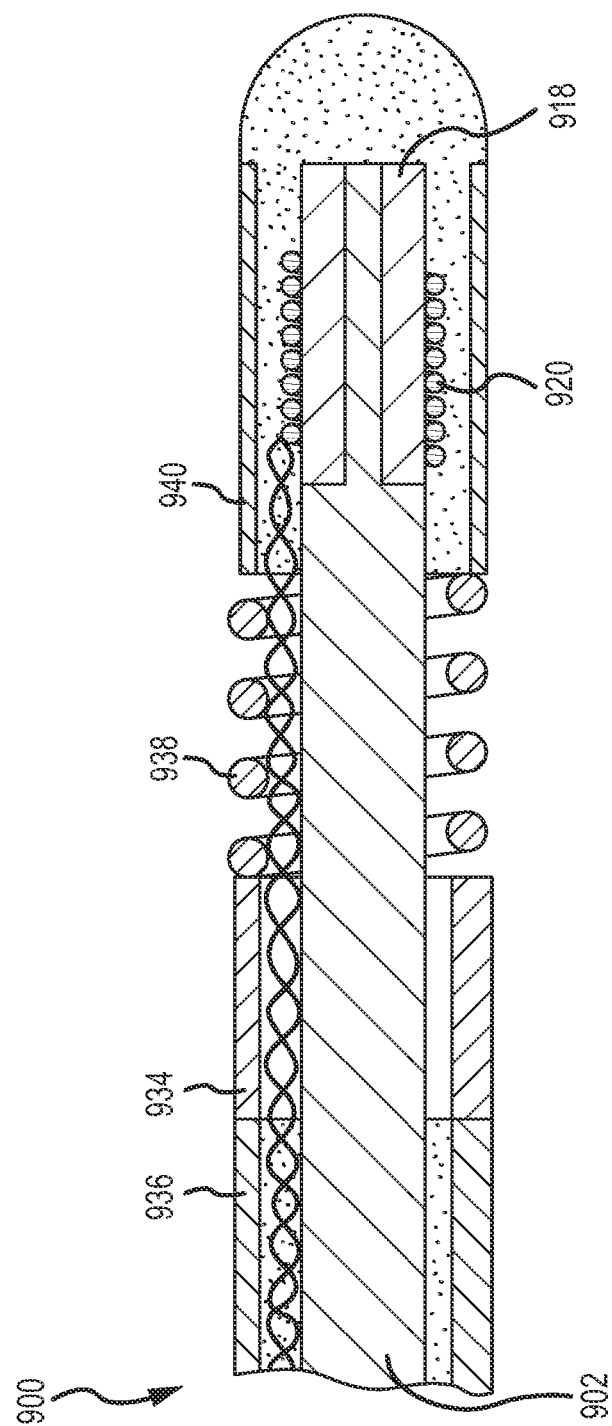
FIG. 11D is cross-sectional view of the guidewire illustrated in FIGS. 11A and 11B at a near final stage of assembly.

With reference to FIG. 11D, which is a schematic illustration of a cross-sectional view of guidewire 900 near a final stage of assembly, in an exemplary embodiment, guidewire 900 may further include one or more thin elastic polymer layers 934 disposed over one or more portions of corewire 902, sensor 920, and/or sensor core 918. In the exemplary embodiment illustrated in FIG. 11D, polymer layer 934 is disposed over a portion of corewire 902, and therefore, twisted pair 931. Polymer layer 934 may comprise a heat shrink tube (such as, for example, a hydrophilic tube) of a few microns thickness, which provides a slick, smooth and lubricious surface. In an embodiment, wherein polymer layer 934 comprises a heat shrink tube, the tube is configured to shrink when exposed to a sufficient amount of heat during a heating process performed during the assembly of guidewire 900. In an exemplary embodiment, polymer layer 934 may comprise an epoxy, cyanoacrylate, or a ultra-violet (UV) curing adhesive. The present disclosure is not meant to be limited to such materials, however, and guidewires having a polymer layer comprising materials other than those specifically identified above remain within the spirit and scope of the present disclosure.

In an exemplary embodiment, and with continued reference to FIG. 11D, guidewire 900 may further include one or more layers of metallic material 936 disposed over one or more portions of corewire 902, sensor 920, and/or sensor core 918. In the exemplary embodiment illustrated in FIG. 11D, guidewire 900 includes one metallic layer 936 disposed over a portion of corewire 902, and therefore, twisted pair 931. In an exemplary embodiment, the metallic layer 936 comprises a hypotube formed of, for example, stainless steel, and is coupled to corewire 902. In one embodiment provided for exemplary purposes only, metallic layer 936 is bonded to corewire 902 using, for example, an adhesive such as those described above. In an exemplary embodiment, metallic layer 936 extends from the proximal end of guidewire 900 to a point at or near the distal end thereof. For example, in the embodiment illustrated in FIG. 11D wherein guidewire 900 includes both polymer layer 934 and metallic layer 936, metallic layer 936 extends from the proximal end of guidewire 900 to polymer layer 934 disposed at or near the distal end of guidewire 900. Accordingly, in such an embodiment, metallic layer 936 is disposed proximate and adjacent to polymer layer 934, and the respective layers may be bonded or otherwise coupled together using, for example, an adhesive such as those described above.

With continued reference to FIG. 11D, in an exemplary embodiment, guidewire 900 may still further include one or more tubular springs 938 covering or circumscribing one or more portions of corewire 902, sensor 920, and/or sensor core 918. Tubular spring 938 is a tube exhibiting lateral flexibility (i.e., perpendicular to the central axis of the tube) made of a metal (e.g., stainless steel, platinum, iridium, nitinol), a flexible polymer tube, or a braided or coiled plastic tube. In an exemplary embodiment, spring 938 comprises a radiopaque material so as to allow for the visualization of the spring, and therefore, the guidewire 900, when used with an x-ray-based visualization system, such as, for example, fluoroscopy. Tubular spring 938, which has a length on the order of centimeters, maintains the outer diameter of guidewire 900 over the length thereof, supports compressive loads, and resists buckling of the guidewire 900 without substantially increasing torsional and bending stiffness.

In an exemplary embodiment, spring 938 is rigidly coupled with sensor 920. More particularly, one end of spring 938 is bonded to sensor 920. As with the coupling of sensor core 918 and corewire 902, spring 938 may be coupled with sensor 920 with an adhesive, such as, for example and without limitation, those described above (e.g., epoxy or cyanoacrylate adhesives). In another exemplary embodiment, and as illustrated in FIG. 11D, rather than coupling one end of spring 938 directly to sensor 920, a cylindrical metal shroud 940 covers sensor 920 and spring 938 is bonded to shroud 940 using, for example, an adhesive such as those described above. In an exemplary embodiment, the end of spring 938 opposite the end bonded to sensor 920 or shroud 940 is coupled with polymer layer 934 or metallic layer 936 described above using, for example, an adhesive such as those described above. In an exemplary embodiment, and as illustrated in FIG. 11D, the same type of adhesive used to bond spring 938 to sensor 920 or shroud 940, for example, may also be used to form a rounded, ball point-type tip at the extreme distal end of the guidewire 900.

In an exemplary embodiment, guidewire 900 may further comprise an outer polymer layer (not shown) extending from the extreme proximal end to the extreme distal end of guidewire such that substantially the entire assembly is covered with the outer polymer layer. The outer polymer layer provides added lubricity and hydrophilic properties, and/or forms a substantially smooth external surface of guidewire 900.

Figure 12:
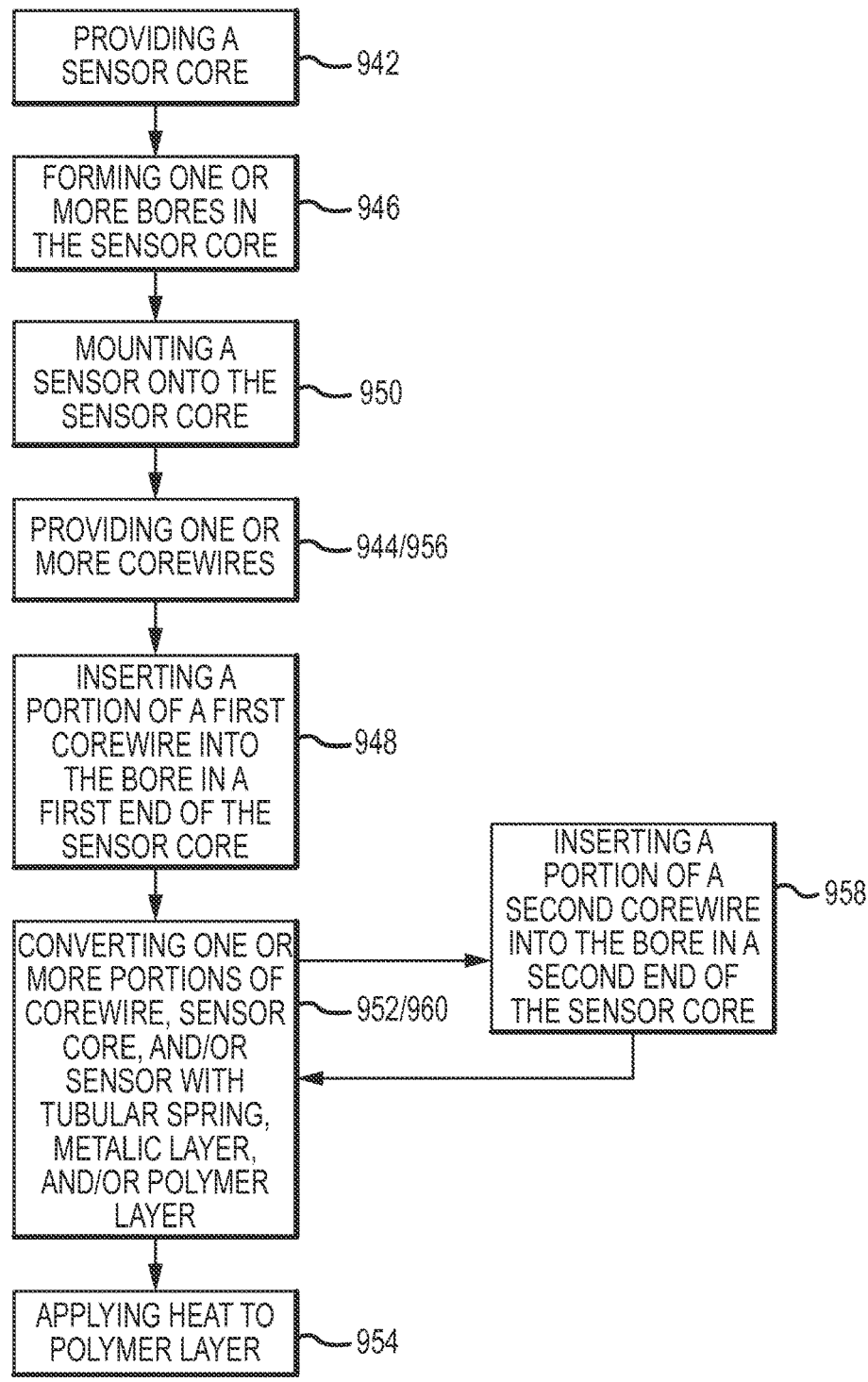
FIG. 12 is a flow chart diagram illustrating an exemplary embodiment of a method of manufacturing the guidewires illustrated in FIGS. 11A-11D in accordance with the present teachings.

In addition to the structure of guidewire 900, it will be appreciated that another aspect of the present disclosure is a method of manufacturing a medical device, such as, for example, guidewire 900. With reference to FIGS. 11A-12, in a exemplary embodiment, the method comprises a step 942 of providing a sensor core, such as, for example, sensor core 918 described above. The method further comprises a step 944 of providing a corewire, such as, for example, corewire 902 described above. The method still further comprises a step 946 of forming a bore, such as, for example, bore 928 described above, in a first end of sensor core 918. In another exemplary embodiment, both ends of the sensor core have a bore therein. In one embodiment, the bore is a through bore extending all the way through the core from the first end through the second end. Alternatively, each end of the sensor core has an independent bore formed therein.

The method yet still further comprises a step 948 of inserting a portion of corewire into the bore in the sensor core. The method may further comprise bonding the corewire with the sensor core using an adhesive such as those described above. In an exemplary embodiment, the method further comprises a step 950 of mounting a sensor, such as, for example, sensor 920 described above, onto the sensor core. In an exemplary embodiment, step 950 may comprise winding a sensor coil onto the sensor core. It will be appreciated by those having ordinary skill in the art, however, that in other exemplary embodiments, the sensor may be mounted to the sensor core using other techniques known in the art. Accordingly, embodiments of the method wherein the sensor is mounted to the sensor core using techniques other than those described with particularity herein, remain within the spirit and scope of the present disclosure. In any embodiment, the method may further comprise a step of connecting a sensor wire, such as, for example, a twisted pair of wires, to the sensor.

In an exemplary embodiment, the method further comprises a step 952 of covering a portion of at least one of the corewire, coupler, and sensor core with an elastic polymer material, a metallic material, and/or a tubular spring, as described in greater detail above.

In an exemplary embodiment wherein the guidewire comprises a layer of elastic polymer material, and the polymer material, in turn, comprises a heat shrink material, the method further comprises a step 954 of applying heat to the guidewire to cause the polymer material to shrink.

In an exemplary embodiment, the method further comprises step 956 of providing a second corewire, such as, for example, corewire 930 described above. In such an embodiment, the method still further comprises a step 950 of inserting a portion of corewire 930 into a bore in the second end of the sensor core. In an exemplary embodiment, the method may further include applying an adhesive to one or both of the corewire 930 and the inner surface of the bore to bond the corewire to the sensor core, as described above. In an exemplary embodiment, the method may still further comprise a step 960 of covering a least a portion of the sensor, sensor core, and/or second corewire with a polymer material, a metallic material, and/or a tubular spring, such as, for example, the polymer layer, metallic layer, and springs described above.

In an exemplary embodiment, and whether the guidewire comprises one or two corewires, the method further comprises covering substantially the entire guidewire assembly with a polymer material to form an outer polymer layer.

It will be appreciated that in other exemplary embodiments, the methodology described above may further include steps not specifically described with respect to FIG. 12, but described elsewhere with respect to FIGS. 11A-11C. Accordingly, embodiments of the method comprising such steps remain within the spirit and scope of the present disclosure.

Although only certain embodiments have been described above with a certain degree of particularity, those skilled in the art could make numerous alterations to the disclosed embodiments without departing from the scope of this disclosure. Joinder references (e.g., attached, bonded, coupled, connected, and the like) are to be construed broadly and may include intermediate members between a connection of elements and relative movement between elements. As such, joinder references do not necessarily infer that two elements are directly connected/coupled and in fixed relation to each other. It is intended that all matter contained in the above description or shown in the accompanying drawings shall be interpreted as illustrative only and not limiting. Changes in detail or structure may be made without departing from the invention as defined in the appended claims.

The invention claimed is:

1. A medical device, comprising:
 a corewire comprising a distal portion;
 a sensor core having a sensor mounted thereon and comprising a proximal portion; and
 a coupler having a first end and a second end, wherein:
  the distal portion of said corewire is disposed within said first end of said coupler, and
  the proximal portion of said sensor core is disposed within said second end of said coupler, said coupler coupling said corewire with said sensor core, wherein said coupler has a shape of a hollow tube comprising a wall with a part of the wall of said hollow tube removed along the length of said hollow tube.

2. The medical device of claim 1, wherein said sensor comprises an electromagnetic field detector.

3. The medical device of claim 1, further comprising at least one of a polymer layer, a metallic layer, and a tubular spring covering at least one portion of at least one of said corewire, said sensor core, said sensor, and said coupler.

4. The medical device of claim 1, wherein:
said coupler has an inner diameter substantially equal to:
i) an outer diameter of said distal portion of said corewire and ii) an outer diameter of said proximal portion of said sensor core disposed within said coupler.

5. The medical device of claim 1 further comprising a tubular spring circumscribing a portion of at least one of said sensor core, coupler, and corewire.

6. The medical device of claim 1 further comprising an elastic polymer layer covering a portion of at least one said sensor core, coupler, and corewire.

7. The medical device of claim 1, wherein said corewire is a first corewire, said coupler is a first coupler, and said proximal portion of said sensor core disposed within said first coupler is a first portion of said sensor core, said medical device further comprising
a second corewire; and
a second coupler having a first end and a second end, wherein:
a second portion of said sensor core is disposed within said first end of said second coupler; and
a portion of said second corewire is disposed within said second end of said second coupler, said second coupler coupling said second corewire with said sensor core.

8. The medical device of claim 7, wherein said second coupler comprises a hollow tube and said hollow tube has an inner diameter substantially equal to: i) an outer diameter of said portion of said second corewire and ii) an outer diameter of said second portion of said sensor core disposed within said second coupler.

9. The medical device of claim 1, wherein said corewire comprises multiple pieces coupled together.

10. The medical device of claim 1, wherein a diameter of said corewire varies from a proximal end to a distal end.

11. The medical device of claim 10, wherein said corewire tapers from the proximal end to the distal end.

12. The medical device of claim 1, wherein a portion of said sensor core is not covered by said sensor.

13. The medical device of claim 1, wherein a diameter of said corewire and a diameter of said sensor core are substantially the same.

14. A method of manufacturing a medical device, said method comprising the steps of:
providing a first corewire comprising a distal portion;
providing a sensor core comprising a first portion, wherein the sensor core is configured to have a sensor mounted thereon;
providing a first coupler configured to couple said first corewire with said sensor core;
mounting said sensor onto said sensor core;
inserting the distal portion of said first corewire into a first end of said first coupler
inserting the first portion of said sensor core into a second end of said first coupler;
providing a second corewire;
providing a second coupler;
inserting a second portion of said sensor core into a first end of said second coupler; and
inserting a portion of said second corewire into a second end of said second coupler.

15. The method of claim 14 further comprising the step of covering at least a portion of at least one of said corewire, said sensor core, said sensor, and said coupler with at least one of a polymer material, a metallic material, and a tubular spring.

16. The method of claim 15 wherein said polymer material comprises a heat shrink tube, said method further comprising the step of applying heat to said polymer material.

17. The method of claim 14 further comprising the step of covering a portion of said corewire, said sensor core, and said coupler with an elastic polymer material.

18. The method of claim 14 further comprising the step of covering a portion of said corewire, said sensor core and said coupler with a tubular spring.

19. The method of claim 14, wherein a portion of said sensor core is not covered by said sensor.

20. A medical device, comprising:
a first corewire comprising a distal portion;
a second corewire;
a sensor core having a sensor mounted thereon and comprising a first portion and a second portion;
a first coupler having a first end and a second end; and
a second coupler having a first end and a second end;
wherein the distal portion of said first corewire is disposed within said first end of said first coupler;
wherein the first portion of said sensor core is disposed within said second end of said first coupler, said first coupler coupling said first corewire with said sensor core;
wherein the second portion of said sensor core is disposed within said first end of said second coupler; and
wherein a portion of said second corewire is disposed within said second end of said second coupler, said second coupler coupling said second corewire with said sensor core.

21. The medical device of claim 20, wherein said second coupler comprises a hollow tube and said hollow tube has an inner diameter substantially equal to: i) an outer diameter of said portion of said second corewire disposed within said second coupler, and ii) an outer diameter of said second portion of said sensor core disposed within said second coupler.

* * * * *